United States Patent
Bouwstra et al.

(10) Patent No.: US 8,357,397 B2
(45) Date of Patent: *Jan. 22, 2013

(54) CONTROLLED RELEASE COMPOSITION COMPRISING A RECOMBINANT GELATIN

(75) Inventors: Jan Bastiaan Bouwstra, Holland (NL); Marc Sutter, Holland (NL); Sebastianus Gerardus Kluijtmans, Holland (NL); Wilhelmus Everhardus Hennink, Holland (NL); Wim Jiskoot, Holland (NL)

(73) Assignee: Fujifilm Manufacturing Europe B.V., Tilburg (NL)

( * ) Notice: Subject to any disclaimer, the term of this patent is extended or adjusted under 35 U.S.C. 154(b) by 498 days.

This patent is subject to a terminal disclaimer.

(21) Appl. No.: 12/528,060

(22) PCT Filed: Feb. 21, 2008

(86) PCT No.: PCT/NL2008/050105
§ 371 (c)(1),
(2), (4) Date: Apr. 25, 2010

(87) PCT Pub. No.: WO2008/103045
PCT Pub. Date: Aug. 28, 2008

(65) Prior Publication Data
US 2010/0203138 A1    Aug. 12, 2010

(30) Foreign Application Priority Data
Feb. 21, 2007   (EP) ..................................... 07102839

(51) Int. Cl.
*A61K 9/26* (2006.01)
(52) U.S. Cl. ..................................................... 424/469
(58) Field of Classification Search .................... 424/469
See application file for complete search history.

(56) References Cited

U.S. PATENT DOCUMENTS

| | | | | |
|---|---|---|---|---|
| 4,808,408 A * | 2/1989 | Baker et al. | | 424/408 |
| 4,855,134 A | 8/1989 | Yamahira et al. | | 424/85.7 |
| 5,002,769 A | 3/1991 | Friedman | | 424/422 |
| 5,023,082 A | 6/1991 | Friedman et al. | | 424/426 |
| 5,399,361 A | 3/1995 | Song et al. | | 424/486 |
| 5,512,301 A | 4/1996 | Song et al. | | 424/484 |
| 5,597,578 A | 1/1997 | Brown et al. | | 424/422 |
| 5,733,994 A | 3/1998 | Koepff et al. | | 527/207 |
| 5,897,879 A | 4/1999 | Friedman et al. | | 424/486 |
| 6,068,854 A | 5/2000 | Wunderlich et al. | | 424/464 |
| 6,140,072 A | 10/2000 | Ferrari et al. | | 435/69.1 |
| 6,150,081 A | 11/2000 | Van Heerde et al. | | 430/569 |
| 6,342,250 B1 | 1/2002 | Masters | | 424/484 |
| 6,458,386 B1 | 10/2002 | Schacht et al. | | 424/488 |
| 6,831,058 B1 | 12/2004 | Tabata et al. | | 514/2 |
| 6,992,172 B1 | 1/2006 | Chang et al. | | 530/354 |
| 7,517,954 B2 | 4/2009 | Bouwstra et al. | | 530/350 |
| 8,101,205 B2 * | 1/2012 | Bouwstra et al. | | 424/469 |
| 2002/0028243 A1 | 3/2002 | Masters | | 424/484 |
| 2002/0106410 A1 | 8/2002 | Masters | | 424/484 |
| 2003/0007991 A1 | 1/2003 | Masters | | 424/423 |
| 2003/0064074 A1 | 4/2003 | Chang et al. | | 424/184.1 |
| 2004/0237663 A1 | 12/2004 | Farber et al. | | 73/861.08 |
| 2005/0058703 A1 | 3/2005 | Chang et al. | | 424/456 |
| 2005/0119170 A1 | 6/2005 | Bouwstra et al. | | 514/12 |
| 2005/0147690 A1 | 7/2005 | Masters et al. | | 424/499 |
| 2005/0208141 A1 | 9/2005 | Farber et al. | | 424/488 |
| 2005/0229264 A1 | 10/2005 | Chang et al. | | 800/8 |
| 2005/0238663 A1 | 10/2005 | Hunt | | 424/239.1 |
| 2006/0024346 A1 | 2/2006 | Brody et al. | | 424/423 |
| 2006/0024361 A1 | 2/2006 | Odidi et al. | | 424/464 |
| 2006/0068013 A1 | 3/2006 | DiTizio et al. | | 424/484 |
| 2006/0121609 A1 | 6/2006 | Yannas et al. | | 435/395 |
| 2006/0147501 A1 | 7/2006 | Hillas et al. | | 424/443 |
| 2006/0177492 A1 | 8/2006 | Yunoki et al. | | 424/445 |
| 2006/0204551 A1 | 9/2006 | Manley et al. | | 424/185.1 |
| 2006/0241032 A1 | 10/2006 | Bouwstra et al. | | 514/12 |
| 2006/0251719 A1 | 11/2006 | Tabata | | 424/468 |
| 2007/0004034 A1 | 1/2007 | Bouwstra et al. | | 435/289.1 |
| 2007/0009580 A1 | 1/2007 | DiCosmo et al. | | 424/443 |
| 2007/0031501 A1 | 2/2007 | Van Es et al. | | 424/488 |
| 2007/0190153 A1 | 8/2007 | Farber | | 424/488 |
| 2007/0196496 A1 | 8/2007 | Farber et al. | | 424/488 |
| 2008/0107666 A1 | 5/2008 | van Es et al. | | 424/185.1 |
| 2008/0113910 A1 | 5/2008 | Bouwstra et al. | | 514/12 |
| 2008/0114078 A1 | 5/2008 | Bouwstra et al. | | 514/774 |

(Continued)

FOREIGN PATENT DOCUMENTS
EP    1 607 085    12/2005
JP   2005-211477    8/2005

(Continued)

OTHER PUBLICATIONS

Meyer et al. 2000, The effect of gelatin corss0linking on the bioequivalence of hard and soft gelatin acetaminophen capsules. Pharmaceutical Research 17(8): 962-966.*
Ofner et al. 2001; Crosslinking studies in gelatin capsules treated with formadehyde and in capsules exposed to elevated temperature and humidity. Journal of Pharmaceutical Sciences. 90(1): 79-88.*
Werten et al., "High-yield Secretion of Recombinant Gelatins by *Pichia pastoris*", Yeast, 15:1087-1096 (1999).
Báez et al., "Recombinant microbial systems for the production of human collagen and gelatin", Appl. Microbiol Biotechnol., 69:245-252 (2005).
Werten et al., "Secreted production of a custom-designed, highly hydrophilic gelatin in *Pichia pastoris*", Protein Engineering, 14(6):447-454 (2001).

(Continued)

*Primary Examiner* — Karen Cochrane Carlson
(74) *Attorney, Agent, or Firm* — Morgan, Lewis & Bockius LLP

(57) ABSTRACT

The invention relates to the field of pharmacology. More specific, the invention relates to a controlled release composition. In one of the embodiments, the invention provides a method for preparing a controlled release composition comprising the steps of:
  providing a mixture of a recombinant gelatin and a pharmaceutical
  chemically cross-linking said recombinant gelatin to obtain a three dimensional network structure.

19 Claims, 3 Drawing Sheets

U.S. PATENT DOCUMENTS

| | | |
|---|---|---|
| 2008/0167446 A1 | 7/2008 | Bouwstra et al. .............. 530/354 |
| 2008/0274957 A1 | 11/2008 | Bouwstra et al. ................ 514/12 |
| 2009/0143568 A1 | 6/2009 | Chang et al. .................. 530/354 |

FOREIGN PATENT DOCUMENTS

| | | |
|---|---|---|
| WO | WO 98/55161 | 12/1998 |
| WO | WO 2004/056976 | 7/2004 |
| WO | WO 2004/085473 | 10/2004 |
| WO | WO 2005/011739 | 2/2005 |
| WO | WO 2007/073190 | 6/2007 |

OTHER PUBLICATIONS

Olsen et al., "Recombinant collagen and gelatin for drug delivery", Advanced Drug Delivery Reviews, Amsterdam, NL, 55(12):1547-1567 (2003).

Sutter et al., "Recombinant gelatin hydrogels for the sustained release of proteins", Journal of Controlled Release, 119:301-312 (2007).

Extracts from gmap-gelatin.com, dated Aug. 25, 2006.

* cited by examiner

```
  1  GAPGAPGLQGAPGLQGMPGERGAAGLPGPK
 31  GERGDAGPKGADGAPGAPGLQGMPGERGAA
 61  GLPGPKGERGDAGPKGADGAPGKDGVRGLA
 91  GPIGPPGERGAAGLPGPKGERGDAGPKGAD
121  GAPGKDGVRGLAGPIGPPGPAGAPGAPGLQ
151  GMPGERGAAGLPGPKGERGDAGPKGADGAP
181  GKDGVRGLAGPI
```

Fig. 3

MFSFVDLRLLLLLLAATALLTHGQEEGQVEGQDEDIPPITCVQNGLRYHDRDVWKPEPCRIC
VCDNGKVLCDDVICDETKNCPGAEVPEGECCPVCPDGSESPTDQETTGVEGPKGDTGPRGP
RGPAGPPGRDGIPGQPGLPGPPGPPGPPGPPGLGGNFAPQLSYGYDEKSTGGISVPGPMGP
SGPRGLPGPPGAPGPQGFQGPPGEPGEPGASGPMGPRGPPGPPGKNGDDGEAGKPGRPGER
GPPGPQGARGLPGTAGLPGMKGHRGFSGLDGAKGDAGPAGPKGEPGSPGENGAPGQMGPRG
LPGERGRPGAPGPAGARGNDGATGAAGPPGPTGPAGPPGFPGAVGAKGEAGPQGPRGSEGP
QGVRGEPGPPGPAGAAGPAGNPGADGQPGAKGANGAPGIAGAPGFPGARGPSGPQGPGGPP
GPKGNSGEPGAPGSKGDTGAKGEPGPVGVQGPPGPAGEEGKRGARGEPGPTGLPGPPGERG
GPGSRGFPGADGVAGPKGPAGERGSPGPAGPKGSPGEAGRPGEAGLPGAKGLTGSPGSPGP
DGKTGPPGPAGQDGRPGPPGPPGARGQAGVMGFPGPKGAAGEPGKAGERGVPGPPGAVGPA
GKDGEAGAQGPPGPAGPAGERGEQGPAGSPGFQGLPGPAGPPGEAGKPGEQGVPGDLGAPG
PSGARGERGFPGERGVQGPPGPAGPRGANGAPGNDGAKGDAGAPGAPGSQGAPGLQGMPGE
RGAAGLPGPKGDRGDAGPKGADGSPGKDGVRGLTGPIGPPGPAGAPGDKGESGPSGPAGPT
GARGAPGDRGEPGPPGPAGFAGPPGADGQPGAKGEPGDAGAKGDAGPPGPAGPAGPPGPIG
NVGAPGAKGARGSAGPPGATGFPGAAGRVGPPGPSGNAGPPGPPGPAGKEGGKGPRGETGP
AGRPGEVGPPGPPGPAGEKGSPGADGPAGAPGTPGPQGIAGQRGVVGLPGQRGERGFPGLP
GPSGEPGKQGPSGASGERGPPGPMGPPGLAGPPGESGREGAPGAEGSPGRDGSPGAKGDRG
ETGPAGPPGAPGAPGAPGPVGPAGKSGDRGETGPAGPAGPVGPAGARGPAGPQGPRGDKGE
TGEQGDRGIKGHRGFSGLQGPPGPPGSPGEQGPSGASGPAGPRGPPGSAGAPGKDGLNGLP
GPIGPPGPRGRTGDAGPVGPPGPPGPPGPPSAGFDFSFLPQPPQEKAHDGGRYYRADD
ANVVRDRDLEVDTTLKSLSQQIENIRSPEGSRKNPARTCRDLKMCHSDWKSGEYWIDPNQG
CNLDAIKVFCNMETGETCVYPTQPSVAQKNWYISKNPKDKRHVWFGESMTDGFQFEYGGQG
SDPADVAIQLTFLRLMSTEASQNITYHCKNSVAYMDQQTGNLKKALLLKGSNEIEIRAEGN
SRFTYSVTVDGCTSHTGAWGKTVIEYKTTKTSRLPIIDVAPLDVGAPDQEFGFDVGPVCFL

```
SEQUENCE LISTING

<160> NUMBER OF SEQ ID NOS: 3

<210> SEQ ID NO 1
<211> LENGTH: 821
<212> TYPE: PRT
<213> ORGANISM: Artificial sequence
<220> FEATURE:
<223> OTHER INFORMATION: HU4 gelatin

<400> SEQUENCE: 1

Gly Pro Pro Gly Glu Pro Gly Pro Thr Gly Leu Pro Gly Pro Pro Gly
1               5                   10                  15

Glu Arg Gly Gly Pro Gly Ser Arg Gly Phe Pro Gly Ala Asp Gly Val
            20                  25                  30

Ala Gly Pro Lys Gly Pro Ala Gly Glu Arg Gly Ser Pro Gly Pro Ala
        35                  40                  45

Gly Pro Lys Gly Ser Pro Gly Glu Ala Gly Arg Pro Gly Glu Ala Gly
    50                  55                  60

Leu Pro Gly Ala Lys Gly Leu Thr Gly Ser Pro Gly Ser Pro Gly Pro
65                  70                  75                  80

Asp Gly Lys Thr Gly Pro Pro Gly Pro Ala Gly Gln Asp Gly Arg Pro
                85                  90                  95

Gly Pro Pro Gly Pro Pro Gly Ala Arg Gly Gln Ala Gly Val Met Gly
            100                 105                 110

Phe Pro Gly Pro Lys Gly Ala Ala Gly Glu Pro Gly Lys Ala Gly Glu
        115                 120                 125

Arg Gly Val Pro Gly Pro Pro Gly Ala Val Gly Pro Ala Gly Lys Asp
    130                 135                 140

Gly Glu Ala Gly Ala Gln Gly Pro Pro Gly Pro Ala Gly Pro Ala Gly
145                 150                 155                 160

Glu Arg Gly Glu Gln Gly Pro Ala Gly Ser Pro Gly Phe Gln Gly Leu
                165                 170                 175

Pro Gly Pro Ala Gly Pro Pro Gly Glu Ala Gly Lys Pro Gly Glu Gln
            180                 185                 190

Gly Val Pro Gly Asp Leu Gly Ala Pro Gly Pro Ser Gly Pro Ala Gly
        195                 200                 205

Glu Pro Gly Pro Thr Gly Leu Pro Gly Pro Pro Gly Glu Arg Gly Gly
    210                 215                 220

Pro Gly Ser Arg Gly Phe Pro Gly Ala Asp Gly Val Ala Gly Pro Lys
225                 230                 235                 240

Gly Pro Ala Gly Glu Arg Gly Ser Pro Gly Pro Ala Gly Pro Lys Gly
                245                 250                 255
```

```
Ser Pro Gly Glu Ala Gly Arg Pro Gly Glu Ala Gly Leu Pro Gly Ala
        260                 265                 270

Lys Gly Leu Thr Gly Ser Pro Gly Ser Pro Gly Pro Asp Gly Lys Thr
            275                 280                 285

Gly Pro Pro Gly Pro Ala Gly Gln Asp Gly Arg Pro Gly Pro Pro Gly
        290                 295                 300

Pro Pro Gly Ala Arg Gly Gln Ala Gly Val Met Gly Phe Pro Gly Pro
305                 310                 315                 320

Lys Gly Ala Ala Gly Glu Pro Gly Lys Ala Gly Glu Arg Gly Val Pro
            325                 330                 335

Gly Pro Pro Gly Ala Val Gly Pro Ala Gly Lys Asp Gly Glu Ala Gly
        340                 345                 350

Ala Gln Gly Pro Pro Gly Pro Ala Gly Pro Ala Gly Glu Arg Gly Glu
            355                 360                 365

Gln Gly Pro Ala Gly Ser Pro Gly Phe Gln Gly Leu Pro Gly Pro Ala
        370                 375                 380

Gly Pro Pro Gly Glu Ala Gly Lys Pro Gly Glu Gln Gly Val Pro Gly
385                 390                 395                 400

Asp Leu Gly Ala Pro Gly Pro Ser Gly Ala Arg Gly Glu Arg Gly Phe
            405                 410                 415

Thr Gly Leu Pro Gly Pro Pro Gly Glu Arg Gly Gly Pro Gly Ser Arg
        420                 425                 430

Gly Phe Pro Gly Ala Asp Gly Val Ala Gly Pro Lys Gly Pro Ala Gly
            435                 440                 445

Glu Arg Gly Ser Pro Gly Pro Ala Gly Pro Lys Gly Ser Pro Gly Glu
        450                 455                 460

Ala Gly Arg Pro Gly Glu Ala Gly Leu Pro Gly Ala Lys Gly Leu Thr
465                 470                 475                 480

Gly Ser Pro Gly Ser Pro Gly Pro Asp Gly Lys Thr Gly Pro Pro Gly
            485                 490                 495

Pro Ala Gly Gln Asp Gly Arg Pro Gly Pro Pro Gly Pro Pro Gly Ala
        500                 505                 510

Arg Gly Gln Ala Gly Val Met Gly Phe Pro Gly Pro Lys Gly Ala Ala
            515                 520                 525

Gly Glu Pro Gly Lys Ala Gly Glu Arg Gly Val Pro Gly Pro Pro Gly
        530                 535                 540

Ala Val Gly Pro Ala Gly Lys Asp Gly Glu Ala Gly Ala Gln Gly Pro
545                 550                 555                 560

Pro Gly Pro Ala Gly Pro Ala Gly Glu Arg Gly Glu Gln Gly Pro Ala
            565                 570                 575

Gly Ser Pro Gly Phe Gln Gly Leu Pro Gly Pro Ala Gly Pro Pro Gly
        580                 585                 590

Glu Ala Gly Lys Pro Gly Glu Gln Gly Val Pro Gly Asp Leu Gly Ala
            595                 600                 605

Pro Gly Pro Ser Gly Pro Ala Gly Glu Pro Gly Pro Thr Gly Leu Pro
        610                 615                 620

Gly Pro Pro Gly Glu Arg Gly Gly Pro Gly Ser Arg Gly Phe Pro Gly
625                 630                 635                 640

Ala Asp Gly Val Ala Gly Pro Lys Gly Pro Ala Gly Glu Arg Gly Ser
            645                 650                 655

Pro Gly Pro Ala Gly Pro Lys Gly Ser Pro Gly Glu Ala Gly Arg Pro
        660                 665                 670

Gly Glu Ala Gly Leu Pro Gly Ala Lys Gly Leu Thr Gly Ser Pro Gly
```

```
                675                 680                 685
Ser Pro Gly Pro Asp Gly Lys Thr Gly Pro Gly Pro Ala Gly Gln
690                 695                 700
Asp Gly Arg Pro Gly Pro Pro Gly Pro Pro Gly Ala Arg Gly Gln Ala
705                 710                 715                 720
Gly Val Met Gly Phe Pro Gly Pro Lys Gly Ala Ala Gly Glu Pro Gly
                725                 730                 735
Lys Ala Gly Glu Arg Gly Val Pro Pro Pro Gly Ala Val Gly Pro
                740                 745                 750
Ala Gly Lys Asp Gly Glu Ala Gly Ala Gln Gly Pro Pro Gly Pro Ala
                755                 760                 765
Gly Pro Ala Gly Glu Arg Gly Glu Gln Gly Pro Ala Gly Ser Pro Gly
                770                 775                 780
Phe Gln Gly Leu Pro Gly Pro Ala Gly Pro Pro Gly Glu Ala Gly Lys
785                 790                 795                 800
Pro Gly Glu Gln Gly Val Pro Gly Asp Leu Gly Ala Pro Gly Pro Ser
                805                 810                 815
Gly Pro Ala Gly Gly
                820

<210> SEQ ID NO 2
<211> LENGTH: 192
<212> TYPE: PRT
<213> ORGANISM: Artificial sequence
<220> FEATURE:
<223> OTHER INFORMATION: CBE

<400> SEQUENCE: 2

Gly Ala Pro Gly Ala Pro Gly Leu Gln Gly Ala Pro Gly Leu Gln Gly
1               5                   10                  15
Met Pro Gly Glu Arg Gly Ala Ala Gly Leu Pro Gly Pro Lys Gly Glu
                20                  25                  30
Arg Gly Asp Ala Gly Pro Lys Gly Ala Asp Gly Ala Pro Gly Ala Pro
                35                  40                  45
Gly Leu Gln Gly Met Pro Gly Glu Arg Gly Ala Ala Gly Leu Pro Gly
                50                  55                  60
Pro Lys Gly Glu Arg Gly Asp Ala Gly Pro Lys Gly Ala Asp Gly Ala
65                  70                  75                  80
Pro Gly Lys Asp Gly Val Arg Gly Leu Ala Gly Pro Ile Gly Pro Pro
                85                  90                  95
Gly Glu Arg Gly Ala Ala Gly Leu Pro Gly Pro Lys Gly Glu Arg Gly
                100                 105                 110
Asp Ala Gly Pro Lys Gly Ala Asp Gly Ala Pro Gly Lys Asp Gly Val
                115                 120                 125
Arg Gly Leu Ala Gly Pro Ile Gly Pro Pro Gly Pro Ala Gly Ala Pro
                130                 135                 140
Gly Ala Pro Gly Leu Gln Gly Met Pro Gly Glu Arg Gly Ala Ala Gly
145                 150                 155                 160
Leu Pro Gly Pro Lys Gly Glu Arg Gly Asp Ala Gly Pro Lys Gly Ala
                165                 170                 175
Asp Gly Ala Pro Gly Lys Asp Gly Val Arg Gly Leu Ala Gly Pro Ile
                180                 185                 190

<210> SEQ ID NO 3
<211> LENGTH: 1464
<212> TYPE: PRT
<213> ORGANISM: Homo sapiens
```

```
<400> SEQUENCE: 3

Met Phe Ser Phe Val Asp Leu Arg Leu Leu Leu Leu Ala Ala Thr
1               5                   10                  15

Ala Leu Leu Thr His Gly Gln Glu Gly Gln Val Glu Gly Gln Asp
                20                  25                  30

Glu Asp Ile Pro Pro Ile Thr Cys Val Gln Asn Gly Leu Arg Tyr His
                35                  40                  45

Asp Arg Asp Val Trp Lys Pro Glu Pro Cys Arg Ile Cys Val Cys Asp
            50                  55                  60

Asn Gly Lys Val Leu Cys Asp Asp Val Ile Cys Asp Glu Thr Lys Asn
65                      70                  75                  80

Cys Pro Gly Ala Glu Val Pro Glu Gly Glu Cys Cys Pro Val Cys Pro
                    85                  90                  95

Asp Gly Ser Glu Ser Pro Thr Asp Gln Glu Thr Thr Gly Val Glu Gly
                100                 105                 110

Pro Lys Gly Asp Thr Gly Pro Arg Gly Pro Arg Gly Pro Ala Gly Pro
                115                 120                 125

Pro Gly Arg Asp Gly Ile Pro Gly Gln Pro Gly Leu Pro Gly Pro Pro
                130                 135                 140

Gly Pro Pro Gly Pro Pro Gly Pro Pro Gly Leu Gly Gly Asn Phe Ala
145                 150                 155                 160

Pro Gln Leu Ser Tyr Gly Tyr Asp Glu Lys Ser Thr Gly Gly Ile Ser
                165                 170                 175

Val Pro Gly Pro Met Gly Pro Ser Gly Pro Arg Gly Leu Pro Gly Pro
                180                 185                 190

Pro Gly Ala Pro Gly Pro Gln Gly Phe Gln Gly Pro Pro Gly Glu Pro
                195                 200                 205

Gly Glu Pro Gly Ala Ser Gly Pro Met Gly Pro Arg Gly Pro Pro Gly
                210                 215                 220

Pro Pro Gly Lys Asn Gly Asp Asp Gly Glu Ala Gly Lys Pro Gly Arg
225                 230                 235                 240

Pro Gly Glu Arg Gly Pro Pro Gly Pro Gln Gly Ala Arg Gly Leu Pro
                245                 250                 255

Gly Thr Ala Gly Leu Pro Gly Met Lys Gly His Arg Gly Phe Ser Gly
                260                 265                 270

Leu Asp Gly Ala Lys Gly Asp Ala Gly Pro Ala Gly Pro Lys Gly Glu
                275                 280                 285

Pro Gly Ser Pro Gly Glu Asn Gly Ala Pro Gly Gln Met Gly Pro Arg
                290                 295                 300

Gly Leu Pro Gly Glu Arg Gly Arg Pro Gly Ala Pro Gly Pro Ala Gly
305                 310                 315                 320

Ala Arg Gly Asn Asp Gly Ala Thr Gly Ala Ala Gly Pro Pro Gly Pro
                325                 330                 335

Thr Gly Pro Ala Gly Pro Pro Gly Phe Pro Gly Ala Val Gly Ala Lys
                340                 345                 350

Gly Glu Ala Gly Pro Gln Gly Pro Arg Gly Ser Glu Gly Pro Gln Gly
                355                 360                 365

Val Arg Gly Glu Pro Gly Pro Pro Gly Pro Ala Gly Ala Ala Gly Pro
                370                 375                 380

Ala Gly Asn Pro Gly Ala Asp Gly Gln Pro Gly Ala Lys Gly Ala Asn
385                 390                 395                 400

Gly Ala Pro Gly Ile Ala Gly Ala Pro Gly Phe Pro Gly Ala Arg Gly
                405                 410                 415
```

```
Pro Ser Gly Pro Gln Gly Pro Gly Gly Pro Gly Pro Lys Gly Asn
            420                 425                 430
Ser Gly Glu Pro Gly Ala Pro Gly Ser Lys Gly Asp Thr Gly Ala Lys
            435                 440                 445
Gly Glu Pro Gly Pro Val Gly Val Gln Gly Pro Gly Pro Ala Gly
450                 455                 460
Glu Glu Gly Lys Arg Gly Ala Arg Gly Glu Pro Gly Pro Thr Gly Leu
465                 470                 475                 480
Pro Gly Pro Pro Gly Glu Arg Gly Gly Pro Gly Ser Arg Gly Phe Pro
                485                 490                 495
Gly Ala Asp Gly Val Ala Gly Pro Lys Gly Pro Ala Gly Glu Arg Gly
                500                 505                 510
Ser Pro Gly Pro Ala Gly Pro Lys Gly Ser Pro Gly Glu Ala Gly Arg
                515                 520                 525
Pro Gly Glu Ala Gly Leu Pro Gly Ala Lys Gly Leu Thr Gly Ser Pro
                530                 535                 540
Gly Ser Pro Gly Pro Asp Gly Lys Thr Gly Pro Pro Gly Pro Ala Gly
545                 550                 555                 560
Gln Asp Gly Arg Pro Gly Pro Pro Gly Pro Pro Gly Ala Arg Gly Gln
                565                 570                 575
Ala Gly Val Met Gly Phe Pro Gly Pro Lys Gly Ala Ala Gly Glu Pro
                580                 585                 590
Gly Lys Ala Gly Glu Arg Gly Val Pro Gly Pro Pro Gly Ala Val Gly
                595                 600                 605
Pro Ala Gly Lys Asp Gly Glu Ala Gly Ala Gln Gly Pro Pro Gly Pro
                610                 615                 620
Ala Gly Pro Ala Gly Glu Arg Gly Glu Gln Gly Pro Ala Gly Ser Pro
625                 630                 635                 640
Gly Phe Gln Gly Leu Pro Gly Pro Ala Gly Pro Pro Gly Glu Ala Gly
                645                 650                 655
Lys Pro Gly Glu Gln Gly Val Pro Gly Asp Leu Gly Ala Pro Gly Pro
                660                 665                 670
Ser Gly Ala Arg Gly Glu Arg Gly Phe Pro Gly Glu Arg Gly Val Gln
                675                 680                 685
Gly Pro Pro Gly Pro Ala Gly Pro Arg Gly Ala Asn Gly Ala Pro Gly
                690                 695                 700
Asn Asp Gly Ala Lys Gly Asp Ala Gly Ala Pro Gly Ala Pro Gly Ser
705                 710                 715                 720
Gln Gly Ala Pro Gly Leu Gln Gly Met Pro Gly Glu Arg Gly Ala Ala
                725                 730                 735
Gly Leu Pro Gly Pro Lys Gly Asp Arg Gly Asp Ala Gly Pro Lys Gly
                740                 745                 750
Ala Asp Gly Ser Pro Gly Lys Asp Gly Val Arg Gly Leu Thr Gly Pro
                755                 760                 765
Ile Gly Pro Pro Gly Pro Ala Gly Ala Pro Gly Asp Lys Gly Glu Ser
                770                 775                 780
Gly Pro Ser Gly Pro Ala Gly Pro Thr Gly Ala Arg Gly Ala Pro Gly
785                 790                 795                 800
Asp Arg Gly Glu Pro Gly Pro Pro Gly Pro Ala Gly Phe Ala Gly Pro
                805                 810                 815
Pro Gly Ala Asp Gly Gln Pro Gly Ala Lys Gly Glu Pro Gly Asp Ala
                820                 825                 830
Gly Ala Lys Gly Asp Ala Gly Pro Pro Gly Pro Ala Gly Pro Ala Gly
```

-continued

```
                835                 840                 845
Pro Pro Gly Pro Ile Gly Asn Val Gly Ala Pro Gly Ala Lys Gly Ala
        850                 855                 860
Arg Gly Ser Ala Gly Pro Gly Ala Thr Gly Phe Pro Gly Ala Ala
865                 870                 875                 880
Gly Arg Val Gly Pro Gly Pro Ser Gly Asn Ala Gly Pro Pro Gly
                885                 890                 895
Pro Pro Gly Pro Ala Gly Lys Glu Gly Gly Lys Gly Pro Arg Gly Glu
            900                 905                 910
Thr Gly Pro Ala Gly Arg Pro Gly Glu Val Gly Pro Pro Gly Pro Pro
                915                 920                 925
Gly Pro Ala Gly Glu Lys Gly Ser Pro Gly Ala Asp Gly Pro Ala Gly
            930                 935                 940
Ala Pro Gly Thr Pro Gly Pro Gln Gly Ile Ala Gly Gln Arg Gly Val
945                 950                 955                 960
Val Gly Leu Pro Gly Gln Arg Gly Glu Arg Gly Phe Pro Gly Leu Pro
                965                 970                 975
Gly Pro Ser Gly Glu Pro Gly Lys Gln Gly Pro Ser Gly Ala Ser Gly
                980                 985                 990
Glu Arg Gly Pro Pro Gly Pro Met Gly Pro Pro Gly Leu Ala Gly Pro
            995                 1000                1005
Pro Gly Glu Ser Gly Arg Glu Gly Ala Pro Gly Ala Glu Gly Ser
        1010                1015                1020
Pro Gly Arg Asp Gly Ser Pro Gly Ala Lys Gly Asp Arg Gly Glu
        1025                1030                1035
Thr Gly Pro Ala Gly Pro Pro Gly Ala Pro Gly Ala Pro Gly Ala
        1040                1045                1050
Pro Gly Pro Val Gly Pro Ala Gly Lys Ser Gly Asp Arg Gly Glu
        1055                1060                1065
Thr Gly Pro Ala Gly Pro Ala Gly Pro Val Gly Pro Ala Gly Ala
        1070                1075                1080
Arg Gly Pro Ala Gly Pro Gln Gly Pro Arg Gly Asp Lys Gly Glu
        1085                1090                1095
Thr Gly Glu Gln Gly Asp Arg Gly Ile Lys Gly His Arg Gly Phe
        1100                1105                1110
Ser Gly Leu Gln Gly Pro Pro Gly Pro Pro Gly Ser Pro Gly Glu
        1115                1120                1125
Gln Gly Pro Ser Gly Ala Ser Gly Pro Ala Gly Pro Arg Gly Pro
        1130                1135                1140
Pro Gly Ser Ala Gly Ala Pro Gly Lys Asp Gly Leu Asn Gly Leu
        1145                1150                1155
Pro Gly Pro Ile Gly Pro Pro Gly Pro Arg Gly Arg Thr Gly Asp
        1160                1165                1170
Ala Gly Pro Val Gly Pro Pro Gly Pro Pro Gly Pro Pro Gly Pro
        1175                1180                1185
Pro Gly Pro Pro Ser Ala Gly Phe Asp Phe Ser Phe Leu Pro Gln
        1190                1195                1200
Pro Pro Gln Glu Lys Ala His Asp Gly Gly Arg Tyr Tyr Arg Ala
        1205                1210                1215
Asp Asp Ala Asn Val Val Arg Asp Arg Asp Leu Glu Val Asp Thr
        1220                1225                1230
Thr Leu Lys Ser Leu Ser Gln Gln Ile Glu Asn Ile Arg Ser Pro
        1235                1240                1245
```

-continued

| | | | | | | | | | | | |
|---|---|---|---|---|---|---|---|---|---|---|---|
| Glu | Gly | Ser | Arg | Lys | Asn | Pro | Ala | Arg | Thr | Cys | Arg | Asp | Leu | Lys |
| | 1250 | | | | 1255 | | | | 1260 | | |
| Met | Cys | His | Ser | Asp | Trp | Lys | Ser | Gly | Glu | Tyr | Trp | Ile | Asp | Pro |
| 1265 | | | | | 1270 | | | | | 1275 | | |
| Asn | Gln | Gly | Cys | Asn | Leu | Asp | Ala | Ile | Lys | Val | Phe | Cys | Asn | Met |
| | 1280 | | | | | 1285 | | | | | 1290 | |
| Glu | Thr | Gly | Glu | Thr | Cys | Val | Tyr | Pro | Thr | Gln | Pro | Ser | Val | Ala |
| | 1295 | | | | | 1300 | | | | | 1305 | |
| Gln | Lys | Asn | Trp | Tyr | Ile | Ser | Lys | Asn | Pro | Lys | Asp | Lys | Arg | His |
| | 1310 | | | | | 1315 | | | | | 1320 | |
| Val | Trp | Phe | Gly | Glu | Ser | Met | Thr | Asp | Gly | Phe | Gln | Phe | Glu | Tyr |
| | 1325 | | | | | 1330 | | | | | 1335 | |
| Gly | Gly | Gln | Gly | Ser | Asp | Pro | Ala | Asp | Val | Ala | Ile | Gln | Leu | Thr |
| | 1340 | | | | | 1345 | | | | | 1350 | |
| Phe | Leu | Arg | Leu | Met | Ser | Thr | Glu | Ala | Ser | Gln | Asn | Ile | Thr | Tyr |
| | 1355 | | | | | 1360 | | | | | 1365 | |
| His | Cys | Lys | Asn | Ser | Val | Ala | Tyr | Met | Asp | Gln | Gln | Thr | Gly | Asn |
| | 1370 | | | | | 1375 | | | | | 1380 | |
| Leu | Lys | Lys | Ala | Leu | Leu | Leu | Lys | Gly | Ser | Asn | Glu | Ile | Glu | Ile |
| | 1385 | | | | | 1390 | | | | | 1395 | |
| Arg | Ala | Glu | Gly | Asn | Ser | Arg | Phe | Thr | Tyr | Ser | Val | Thr | Val | Asp |
| | 1400 | | | | | 1405 | | | | | 1410 | |
| Gly | Cys | Thr | Ser | His | Thr | Gly | Ala | Trp | Gly | Lys | Thr | Val | Ile | Glu |
| | 1415 | | | | | 1420 | | | | | 1425 | |
| Tyr | Lys | Thr | Thr | Lys | Thr | Ser | Arg | Leu | Pro | Ile | Ile | Asp | Val | Ala |
| | 1430 | | | | | 1435 | | | | | 1440 | |
| Pro | Leu | Asp | Val | Gly | Ala | Pro | Asp | Gln | Glu | Phe | Gly | Phe | Asp | Val |
| | 1445 | | | | | 1450 | | | | | 1455 | |
| Gly | Pro | Val | Cys | Phe | Leu |
| | 1460 | | | | |

CONTROLLED RELEASE COMPOSITION COMPRISING A RECOMBINANT GELATIN

This is a 371 filing based on PCT/NL2008/050105 filed Feb. 21, 2008 and claiming priority from European Application No. 07102839.3, filed Feb. 21, 2007.

FIELD OF INVENTION

The invention relates to the field of pharmacology. More specific, the invention relates to a controlled release composition, a pharmaceutical composition comprising the controlled release composition, a pharmaceutical article comprising the controlled release composition, and to a method for preparing the controlled release composition as well as to the use of a recombinant gelatin for producing the controlled release composition.

PRIOR ART

Maintaining pharmacologically active concentrations of parenterally administered therapeutic proteins over a prolonged period of time can be achieved by structural alteration of the proteins to increase their circulation time and by the use of controlled release formulations. For some proteins, e.g. tissue plasminogen activator, erythropeotin, and interferon, alteration of the protein native structure was a successful approach. In many situations however, the development of a slow release formulation is the more feasible approach. At present, slow release formulations are frequently prepared by encapsulating the protein in a polymeric matrix, from which it is released within several days, weeks, or months, either by diffusion or degradation of the matrix. The preservation of native structure and functionality of the encapsulated protein is a major issue in the development of slow release formulations. Furthermore, the formulations should be well tolerated and with regard to parenteral administration, it is often preferable that they be entirely biodegradable to avoid surgical removal of empty matrices.

Hydrogels are specific types of matrix systems that are attractive for the controlled release of therapeutic proteins. They are three dimensional network structures formed after physical or chemical cross-linking of hydrophilic polymers, and contain large amounts of water. It is possible to develop hydrogels as implantable or injectable, in-situ gelling systems. The hydrophilicity of hydrogels has been shown to be favorable for preserving the native structure and functionality of the incorporated protein. The high water content and soft consistency of hydrogels minimizes mechanical irritation upon administration. Furthermore, it has been shown that hydrogels are well tolerated and biocompatible in-vivo. Depending on the type of polymer and the type of cross-link, they are also biodegradable.

Polymers for the preparation of hydrogels are commonly classified as natural derived or synthetic. Natural derived polymers like dextrans and gelatins have been used for the development of hydrogels for protein delivery, because these polymers are biocompatible and biodegradable. However, adaptation of natural derived polymers is limited to the chemical derivatization of functional groups in the polymer backbone.

SUMMARY OF THE INVENTION

The present invention provides a method for preparing a controlled release composition comprising the steps of:

providing a mixture of a recombinant gelatin and a pharmaceutical cross-linking said recombinant gelatin in said mixture to provide a three dimensional network structure wherein the said pharmaceutical is entrapped.

The terms "entrap" or "entrapped" as used herein refer to the fact that the pharmaceutical is held captured (in a space defined) by individually crosslinked gelatin molecules. This term is different from the term "encapsulated", wherein the pharmaceutical is contained in a location that is surrounded, enclosed or enveloped by the encapsulating material.

The use of the recombinant gelatin for this application has many advantages, which are especially due to the specific character of these gelatins. The invention is furthermore directed to a controlled release composition comprising a cross-linked recombinant gelatin and a pharmaceutical and to a pharmaceutical composition and a pharmaceutical article using the inventive controlled release composition. The invention is also directed to a method of treating a subject with an effective amount of the inventive controlled release composition.

DETAILED DESCRIPTION

Hydrogels are specific types of three dimensional matrix systems that are attractive for the controlled release of therapeutic proteins. Polymers for the preparation of hydrogels are commonly classified as natural derived or synthetic. Natural derived polymers like dextrans and gelatins have been used for the development of hydrogels for protein delivery, because these polymers are biocompatible and biodegradable Using the natural derived polymers in preparing hydrogels for controlled release application has as disadvantage, that upon administration the release of the pharmaceutical component is far from linear and quite often at the initial stages the release is boosted to such an extend, that the controlled release product cannot be used. It is a further disadvantage, that the activity of the pharmaceutical might be negatively influenced upon formation of the hydrogel. The latter might be caused by the loss of the molecular conformation of the pharmaceutical and could even cause immunogenic responses. These adverse effects are generally attributed to the inhomogeneous nature of the natural derived polymers, i.e. their very broad molecular weight distribution and potential presence of animal derived impurities. The latter is becoming of growing importance with respect to safety of pharmaceutical products.

The present invention is directed to circumvent these disadvantages of the prior art.

Recently, protein polymers like gelatin and collagen that were originally natural derived are also produced biotechnologically by the use of recombinant DNA technology. In a preferred embodiment recombinant gelatins are produced using *Pichia pastoris* as an expression system. Even when the amino acid sequence of recombinant gelatins is chosen to be equal to that of non-recombinant gelatins their chemical structure is not precisely identical to that of non-recombinant gelatins, because the post-translational modifications in *Pichia pastoris* and animal cells are different. The hydroxylation of praline residues, which is important for secondary structure and triple-helix formation of gelatins, does not occur, because *Pichia pastoris* does not contain the enzyme prolyl-4-hydroxylase. The hydroxylation of lysine residues and the glycosilation of hydroxylysine residues do also not occur in *Pichia pastoris*. Glycosilation of recombinant gelatins, e.g. at serine residues, is possible.

As a consequence of the numerous possible differences between non-recombinant and recombinant gelatins, the latter should be regarded as a new class of biopolymers.

An important feature of controlled release compositions is, that the polymer used for the hydrogel preparation should be biodegradable and as such does not require invasive surgical methods to be removed after complete release of pharmaceuticals. Moreover biodegradability could be required to release the pharmaceutical used in the composition. A priori it is not obvious whether recombinant gelatins will be broken down by the same mechanisms causing degradation of natural gelatins. It is known that natural gelatins and collagens are degraded in the human body by proteases and more specifically matrix-metalloproteinases (MMP). Matrix metalloproteinases (MMP's) are zinc-dependent endopeptidases. The MMP's belong to a larger family of proteases known as the metzincin superfamily. Collectively they are capable of degrading all kinds of extracellular matrix proteins, but also can process a number of bioactive molecules. An important group of MMP's are the collagenases. These MMP's are capable of degrading triple-helical fibrillar collagens into distinctive ¾ and ¼ fragments. These collagens are the major components of bone and cartilage, and MMP's are the only known mammalian enzymes capable of degrading them. Traditionally, the collagenases are MMP-1 (Interstitial collagenase), MMP-8 (Neutrophil collagenase), MMP-13 (Collagenase 3) and MMP-18 (Collagenase 4). Another important, group of MMP's is formed by the gelatinases. The main substrates of these MMP's are type IV collagen and gelatin, and these enzymes are distinguished by the presence of an additional domain inserted into the catalytic domain. This gelatin-binding region is positioned immediately before the zinc binding motif, and forms a separate folding unit which does not disrupt the structure of the catalytic domain. The two members of this sub-group are: MMP-2 (72 kDa gelatinase, gelatinase-A) and MMP-9 (92 kDa gelatinase, gelatinase-B).

Surprisingly, the present invention discloses that a recombinant gelatin that does not comprise a known cleavage site for MMP is enzymatically degradable by human matrix metalloproteinase 1 (MMP1). Apparently many more types of (recombinant) gelatin can be applied than predicted so far. Based on this finding, the inventors have developed useful applications in respect of recombinant gelatins.

Recombinant gelatins are particularly attractive as polymers for the development of protein delivery systems for several reasons. The biotechnological production eliminates the risk of prion contaminations, which are possibly present in animal source gelatins. Recombinant gelatins have well defined molecular weights, determined by the gelatin gene that is expressed. Furthermore, recombinant DNA technology opens the possibility to manipulate the chemical makeup of gelatins through modifying or designing the amino acid sequence. This is potentially useful for defining the number and the positions of amino acids involved in cross-linking, or for steering the biodegradability of gelatins by introducing amino acid sequences that are substrates (cleavage sites) for proteases as discussed above.

In a first embodiment, the invention provides a method for preparing a controlled release composition comprising the steps of:
providing a mixture, for instance a solution, comprising a recombinant gelatin and a pharmaceutical
cross-linking said recombinant gelatin in the mixture to obtain a three dimensional network structure.

The obtained three dimensional (3-D) network structure is a consistent network of cross-linked polymer chains which when wet are usually having elastic properties (hence having a storage modulus) rather than being viscous.

A controlled release composition (or system) or a hydrogel (the terms are used interchangeably herein) typically refers to a network of polymer chains comprising a substantial amount of water. Depending on the application, i.e. desired release profile of the included pharmaceutical and mechanical stress to which the hydrogel is subjected, several types of hydrogels can be used. For example hydrogels that are very stiff and inelastic containing 40%-60% of water, hydrogels that are elastic but still rigid containing 60-85% of water, and hydrogels that are soft and very elastic containing 85-99% of water. Hydrogels can be prepared from natural or synthetic polymers. Hydrogel-forming polymers are polymers that are capable of absorbing a substantial amount of water to form an elastic or inelastic gel. Examples of synthetic polymers are polyethylene oxide, poly(2-acrylamido-2-methyl-1-propanesulfonic acid), polyvinylpyrrolidone, polyacrylamides, polyvinyl alcohol, sodium polyacrylate, acrylate polymers and copolymers with an abundance of hydrophilic groups. Examples of natural polymers and their derivatives are polysaccharides such as dextrin, dextran, chitin, chitosan, carrageenan and agar, cellulose and its derivatives, alginate, natural gums such as xanthan gum, locust bean gum, and collagen and its derivatives such as gelatin.

Recombinant gelatin (also referred to as recombinant collagen or recombinant collagen-like peptides) typically refers to one or more gelatin or gelatin-like polypeptides produced by recombinant methods, such as by expression of a nucleotide encoding the peptide in a micro-organism, insect, plant or animal host. Such peptides are characterized by comprising Gly-Xaa-Yaa triplets wherein Gly is the amino acid glycine and Xaa and Yaa can be the same or different and can be any known amino acid. At least 40% of the amino acids are preferably present in the form of consecutive Gly-Xaa-Yaa triplets. More preferably at least 60%, even more preferably at least 80% or even more than 90% of the amino acids are present in the form of Gly-Xaa-Yaa triplets. Preferably, the peptides have a molecular weight of about 2.5 kD or more. More preferred are molecular weights of between about 2.5 to about 100 kD or between about 15 to about 90 kD. Even more preferred are molecular weights of recombinant gelatin of between about 30 kD and about 80 kD, most preferably 31 kD or higher. Recombinant gelatin can be produced as described in EP-A-0926543 and EP-A-1014176 or as described in U.S. Pat. No. 6,150,081. Most preferred gelatins are CBE (FIG. 2) or multimers thereof, such as trimers or pentamers which only provide for a peptide of longer (3× or 5×) the length of CBE.

Recombinant gelatins can be derived for example from any type of collagen, such as collagen type I, II, III, or IV. In a preferred embodiment the recombinant gelatins are derived from human collagen to avoid potential adverse immunogenic responses. In other examples the recombinant gelatin might be designed to meet specific application needs with respect to interaction with the tissue in which the hydrogel is placed For example recombinant gelatins might be enriched in RGD motifs (i.e arginine-glycine-aspartic acid sequence). RGD motives in proteins are well-known to affect and enhance cell binding properties. Other examples that may be particularly beneficial are recombinant gelatins that are non-glycosylated. In these specific gelatins all known glycosylation sites for the *Pichia* expression system have been omitted as described in patent specification WO2006/091099.

There are different ways in which a solution of a recombinant gelatin and a pharmaceutical can be prepared. For example, one can first prepare a solution of a recombinant, gelatin by dissolving a recombinant gelatin in a suitable solvent and subsequently adding or dissolving a pharmaceutical to or in the prepared recombinant gelatin solution. Aqueous solutions are most preferred. Mixtures with water miscible organic solvents such as tetrahydrofurane, acetone or ethanol can also be used. Other solvents that may be applied are glycol, tetrafluorethane, dimethylsulfoxide, N,N-dimethyl-formamide, and N-Methyl-Pyrrolidinone (NMP). All solvents can be used alone or as mixture with other solvents. In some cases a specific pH is required, for example to steer the electrostatic interaction between the gelatin matrix and the pharmaceutical. The pH can be adjusted using any acid or base. Furthermore solutions can be buffered using all commonly known organic or anorganic buffers. It is clear that if the recombinant gelatin is already present as a solution the first part of this example can be skipped or replaced by diluting said recombinant gelatin in a suitable diluent. In another example one first prepares a solution of a pharmaceutical by adding or dissolving said pharmaceutical to or in a suitable diluent or solvent and subsequently adding or dissolving a recombinant gelatin to or in the solution comprising said pharmaceutical. In yet another example, one adds and/or dissolves a recombinant gelatin and a pharmaceutical at the same time to or in a suitable diluent or solvent.

The pharmaceutical does not always need to be dissolved. In case the solubility of the pharmaceutical in the solvent system used is limited it is also possible to use particle suspensions of the pharmaceutical. These particles suspensions can be already preformed and added to the gelatin solution or vice versa, or be formed, i.e. precipitated, in the gelatin solution.

After cross-linking said recombinant gelatin a three dimensional network structure/controlled release composition is obtained. The obtained three dimensional network structure comprises a matrix that comprises/entraps the used pharmaceutical. The pharmaceutical subsequently releases from the three dimensional network structure within several days, weeks, or months by diffusion upon degradation of the matrix.

Depending on the subsequent use of the obtained controlled release composition, the method of the invention may include a drying step, i.e. in a preferred embodiment the invention provides a method for preparing a controlled release composition comprising the steps of:

providing a mixture (such as a solution) comprising a recombinant gelatin and a pharmaceutical;

cross-linking said recombinant gelatin in said mixture to obtain a three dimensional network structure wherein the pharmaceutical is entrapped in the network structure;

drying the obtained three dimensional network structure.

Essentially when the pharmaceutical is entrapped in the network structure (gel matrix), the network and the pharmaceutical form a solid/gel mixture.

The entrapped pharmaceutical is preferably essentially prevented to diffuse out from the crosslinked gelatine matrix due to its entrapment therein, and is preferably essentially only released when this 3D network structure when the crosslinked gelatine is degraded (e.g. in vivo).

The rate at which the pharmaceutical is released from the controlled release composition of the present invention (i.e. the release rate) is such that preferably less than 50%, more preferably less than 40%, even more preferably less than 30%, 20%, 10%, 5%, 4%, 3%, 2% or 1% of the fraction of the pharmaceutical entrapped in the controlled release composition is released in a period of 24 hours when the controlled release composition is placed in aqueous solution (for instance as described in the Examples). Such slow release rates are indicative of degradation-governed release, rather than diffusion-governed release.

Depending on the application the controlled release composition can be obtained as a gel or elastic semi-solid in various shapes by pouring it in molds and subsequent chemical cross-linking. Furthermore controlled release particles may be obtained by emulsifying the controlled release composition and isolating the formed emulsion droplets after cross-linking as more or less solid particles. Another way to obtain controlled release particles is by spray drying. Particle size may range from 0.1 micrometer to 1000 micrometer, but depending on the application and the desired release profile, more specific ranges could be selected. In case injectable formulations are used the particle size preferably should not exceed 200 micrometer. Furthermore the controlled release compositions may be cast into films or sheets. Examples of suitable casting techniques include spin coating, gravure coating, flow coating, spray coating, coating with a brush or roller, screen printing, knife coating, curtain coating, slide curtain coating, extrusion, squeege coating, and the like. Film or sheet thickness may range from 1 micrometer up to 1 centimeter. For example in case of wound dressings thicknesses of 1 millimeter to 1 centimeter are preferred, while for coatings of medical devices such as stents or vascular grafts or other implants coating thicknesses up to 1 mm are preferable. Drying of the compostions may be performed by common techniques such as air drying, vacuum drying, freeze drying, or spray drying.

The cross-linking process by which the crosslinked gelatine is prepared is essentially chemical. The term chemical crosslinking as used herein refers to the fact that the crosslinking is achieved by the addition of cross-linking agents or the modification of the gelatin with cross-linkable groups. It must be expressly noted that the term crosslinking as used herein does not refer to the crosslinking between lysine residues in hydroxylated gelatin. In natural collagens (e.g. from bone or hide) from which natural gelatins are derived a certain amount of the proline and lysine residues are hydroxylated by hydroxylases. The resulting hydroxylated lysyl residues present within and between individual collagen molecules can be biosynthetically crosslinked in vivo thereby crosslinking the collagens into fibrillar structures. While the derived natural gelatin lost the fibrillar structure of collagen, parts of the biosynthetic crosslinks will remain. This type of crosslinking is not desirable, as it cannot be controlled. Moreover, this type of crosslinking is inherently present in natural gelatins, that is, from the moment of its production, and to varying degrees. In the present invention, the crosslinking should only occur when the gelatin is mixed with the pharmaceutical active. Hence, it is desirable that the commencement of crosslinking can be controlled, as well as the level thereof. Hence, a gelatin used in aspects of the present invention preferably is a recombinant gelatin more preferably produced in a expression system that lacks the biosynthetic enzymes for hydroxylation and biosynthetic crosslinking of lysine residues and therefore comprises essentially no hydroxylysine crosslinks (is essentially free of hydroxylysine crosslinks). Also the gelatin used in aspects of the present invention is essentially free of hydroxyproline residues.

Depending on for example the stability of the used pharmaceutical during the process of cross-linking it may also be possible to first prepare the cross-linked hydrogel and optionally dry it in the absence of the pharmaceutical and then include the pharmaceutical. Upon cross-linking of the matrix the therapeutic protein (TP) can be co-cross-linked resulting in activity loss and in worst case toxic effects. Hence it has advantages to incorporate the TP after preparing the hydrogel.

Several techniques may be applied to incorporate the pharmaceutical in the (dried) hydrogel such as submersing the (dried) hydrogel in solution of a pharmaceutical or by dripping solution of the pharmaceutical on top.

Upon administration of a controlled release composition to a subject, the controlled release composition is exposed to a pH of about 7.4, the physiological pH. It was found, that the very good release characteristics could be obtained for pharmaceuticals having a pI above 7.4 in case the pI of the recombinant gelatin matrix is below 7.4, while the same good results were obtained for pharmaceuticals having a pI below 7.4 with recombinant gelatin matrices having a pI above 7.4. For the loading of the hydrogel preferably a pH should be chosen such that the pI of the recombinant gelatin matrix is above or below this pH, in case the pI of the pharmaceutical is respectively below and above this pH.

Besides optimising the load also the stability of the pharmaceutical/therapeutic protein can be safeguarded. Although chemical modification can also be used to change the charge of the matrix polymer this would create risks with respect to chemical residuals and toxic behaviour of the modified gelatin itself (e.g phtalated gelatins or amine enriched gelatins) and of the stability of proteins included.

The recombinant gelatin used in a method of the invention can be selected from a vast array of recombinant gelatins, for example a recombinant gelatin based on mammalian collagen including human collagen type I, II, III, or IV. As described above, a recombinant gelatin can be produced in any suitable (over)expression system, for example expression in yeast, bacteria, fungi or plants. It is clear to the skilled person that the use of a certain expression system might impose specific properties on the produced recombinant gelatin, for example a different glycosylation pattern (if compared to a natural variant). The amount and pattern of glycosylation can have detrimental effects on the immuno-tolerance to a controlled release article according the invention, therefore the preferred embodiment of the invention comprises recombinant gelatins with essentially no glycosylation.

An important advantage of the use of a recombinant gelatin is that well-defined controlled release compositions can be prepared. Also the constant quality (for example the purity and well-defined molecular weight) of the recombinant gelatins compared to animal derived gelatins contributes to the quality of the pharmaceutical in the controlled release composition.

Another important advantage of a recombinant gelatin is that the amino acid sequence can be manipulated to create certain characteristics. Examples of characteristics that can now be manipulated are (i) the amount of cross-linkable amino acids (for example the amount of (hydroxy)lysines), (ii) the glycosylation pattern (for example the absence of threonine and/or serine amino acids in certain triplets results in the absence of glycosylation), (iii) the size of the recombinant gelatin, (iv) the charge density of the recombinant gelatin can be amended (for example charged amino acids, such as asparagine (Asn), aspartic acid (Asd), glutamine (Gln), glutamic acid (Glu) or lysine (Lys) can be introduced or left out) and as such the loading and release of a pharmaceutical (especially a therapeutic protein) can be influenced or (v) the biodegradability can be amended by the presence or absence of cleavage sites for metalloproteases.

Depending on the specific need, a method of the invention can include steps like, selecting a recombinant gelatin based on the amount of cross-linkable amino acids present in said recombinant gelatin or genetically modifying a recombinant gelatin to increase (or decrease) the amount of (hydroxy) lysine residues in said recombinant gelatin.

In a preferred embodiment, the invention provides a method for preparing a controlled release composition comprising the steps of:

providing a solution of a recombinant gelatin and a pharmaceutical (chemically) cross-linking said recombinant gelatin to obtain a three dimensional network structure, in which said recombinant gelatin is mammalian-like, preferably human. Mammalian-like gelatin is defined as being for at least 60%, more preferable for at least 80%, most preferably for at least 90% identical to mammalian collagen sequences. A starting point for preparing a recombinant mammalian-like gelatin is for example the human Col1A1 sequence. However, it is also possible to use other mammalian collagen sequences to start with.

As mentioned above one important characteristic of a recombinant gelatin is the amount of cross-linkable amino acids, such as the amount of (hydroxy)-lysine groups and the amount of carboxylic acid groups derived from aspartic and glutamic acid. In a preferred embodiment, the invention provides a method for preparing a controlled release composition comprising the steps of:

providing a solution of a recombinant gelatin and a pharmaceutical (chemically) cross-linking said recombinant gelatin to obtain a three dimensional network structure, wherein said recombinant gelatin comprises at least 0.05 mmol/g lysine or hydroxylysine groups prior to cross-linking.

Preferably said recombinant gelatin comprises at least 0.10 mmol/g lysine or hydroxylysine groups, more preferably at least 0.20 mmol/g to obtain a suitable structure after cross-linking. Also higher lysine or hydroxylysine contents of around 0.40 or up to 0.60 or 0.80 mmol/g may be applied depending on the desired three dimensional network structure.

It is clear that the amount of cross-linkable group has an effect on the degree of cross-linking. If more cross-linkable groups are available, the amount of cross links can in principle be higher if compared to a situation in which less linkable groups are present. The lower limit of cross-linkable groups is that amount that still can result in the formation of a gel. The amount of cross-linkable groups in principle also determines the mesh size which is a measure of the average "pore size" of the entangled/cross-linked gelatin network at physiological conditions (pH 7.4, 37° C. and 300 mOsm/L). Finally, the amount of cross-linked groups determine the biodegradability of the formed controlled release composition. By using a recombinant gelatin, the amount of cross-linkable groups can be influenced and thus the gel mesh size and biodegradability can be manipulated.

In case of chemical cross-linking, the used recombinant gelatin is for example provided with a (chemical) linker and subsequently subjected to a linking reaction. The invention therefore provides a method for preparing a controlled release composition comprising the steps of:

providing a solution of a recombinant gelatin and a pharmaceutical chemically cross-linking said recombinant gelatin to obtain a three dimensional network structure, wherein said recombinant gelatin is chemically modified with a cross-linkable group.

Said cross-linkable group may be selected from, but is not limited to epoxy compounds, oxetane derivatives, lactone derivatives, oxazoline derivatives, cyclic siloxanes, or ethenically unsaturated compounds such as acrylates, methacrylates, polyene-polythiols, vinylethers, vinylamides, vinylamines, allyl ethers, allylesters, allylamines, maleic acid derivatives, itacoic acid derivatives, polybutadienes and styrenes. Preferably as the cross-linkable group (meth)acrylates are used, such as alkyl-(meth)acrylates, polyester-(meth) acrylates, urethane-(meth)acrylates, polyether-(meth)acrylates, epoxy-(meth)acrylates, polybutadiene-(meth)acrylates, silicone-(meth)acrylates, melamine-(meth)acrylates, phosphazene-(meth)acrylates, (meth)acrylamides and combinations thereof because of their high reactivity. Even more preferably said cross-linkable group is a methacrylate and hence in preferred aspects of the invention use is made of methacrylated recombinant gelatin. Such a methacrylated recombinant gelatin is very useful in the preparation of a controlled release composition. Generally, the linking groups (for example methacrylate) are coupled to the recombinant gelatin and cross-linking is obtained by redox polymerisation (for example by subjection to a chemical initiator such as the combination potassium peroxodisulfate (KPS)/N,N,N',N' tetramethylethyenediamine (TEMED)) or by radical polymerisation in the presence of an initiator for instance by thermal reaction of by radiation such as UV-light).

Depending on the type of gelatin (the number of cross-linkable groups) and the method of cross-linking selected a certain cross-link density can be obtained which is strongly related to the average mesh size that can be achieved. When a cross-linking group is coupled to the gelatin in a separate step and for the hydrogel a dense network structure is desired it is preferred that at least 50% of the cross-linkable groups in the gelatin are activated, more preferably at least 75%. Most preferably the degree of substitution is close to 100%.

Photo-initiators may be used in accordance with the present invention and can be mixed into the solution of the recombinant gelatin. Photo-initiators are usually required when the mixture is cured by UV or visible light radiation. Suitable photo-initiators are those known in the art such as radical type, cation type or anion type photo-initiators.

Examples of radical type I photo-initiators are α-hydroxyalkylketones, such as 2-hydroxy-1-[4-(2-hydroxyethoxy) phenyl]-2-methyl-1-propanone (Irgacure™ 2959: Ciba), 1-hydroxy-cyclohexyl-phenylketone (Irgacure™ 184: Ciba), 2-hydroxy-2-methyl-1-phenyl-1-propanone (Sarcure™ SR1173: Sartomer), oligo[2-hydroxy-2-methyl-1-{4-(1-methylvinyl)phenyl}propanone] (Sarcure™ SR1130: Sartomer), 2-hydroxy-2-methyl-1-(4-tert-butyl-)phenylpropan-1-one, 2-hydroxy-[4'-(2-hydroxypropoxy)phenyl]-2-methylpropan-1-one, 1-(4-Isopropylphenyl)-2-hydroxy-2-methyl-propanone (Darcure™ 1116: Ciba): α-aminoalkylphenones such as 2-benzyl-2-(dimethylamino)-4'-morpholinobutyrophenone (Irgacure™ 369: Ciba), 2-methyl-4'-(methylthio)-2-morpholinopropiophenone (Irgacure™ 907: Ciba); α,α-dialkoxyacetophenones such as α,α-dimethoxy-α-phenylacetophenone (Irgacure™ 651: Ciba), 2,2-diethyoxy-1,2-diphenylethanone (Uvatone™ 8302: Upjohn), α,α-diethoxyacetophenone (DEAP: Rahn), α,α-di-(n-butoxy)acetophenone (Uvatone™ 8301: Upjohn); phenylglyoxolates such as methylbenzoylformate (Darocure™ MBF: Ciba); benzoin derivatives such as benzoin (Esacure™ BO: Lamberti), benzoin alkyl ethers (ethyl, isopropyl, n-butyl, iso-butyl, etc.), benzylbenzoin benzyl ethers, Anisoin; mono- and bis-Acylphosphine oxides, such as 2,4,6-trimethylbenzoyl-diphenylphosphine oxide (Lucirin™ TPO: BASF), ethyl-2,4,6-trimethylbenzaylphenylphosphinate (Lucirin™ TPO-L: BASF), bis(2,4,6-trimethylbenzoyl)-phenylphosphine oxide (Irgacure™ 819: Ciba), bis(2,6-dimethoxybenzoyl)-2,4,4-trimethyl-pentylphosphineoxide-(Irgacure 1800 or 1870). Other commercially available photo-initiators are 1-[4-(phenylthio)-2-(O-benzoyloxime)]-1,2-octanedione (Irgacure OXE01), 1-[9-ethyl-6-(2-methylbenzoyl)-9H-carbazol-3-yl]-1-(O-acetyloxime)ethanone (Irgacure OXE02), 2-hydroxy-1-{4-[4-(2-hydroxy-2-methyl-propionyl)-benzyl]-phenyl}-2-methyl-propan-1-one (Irgacure 127), oxy-phenyl-acetic acid 2-[2 oxo-2-phenyl-acetoxy-ethoxy]-ethyl ester (Irgacure 754), oxy-phenyl-acetic-2-[2-hydroxy-ethoxy]-ethyl ester (Irgacure 754), 2-(dimethylamino)-2-(4-methylbenzyl)-1-[4-(4-morpholinyl)phenyl]-1-butanone (Irgacure 379), 1-[4-[4-benzoylphenyl)thio]phenyl]-2-methyl-2-[(4-methylphenyl)sulfonyl)]-1-propanone (Esacure 1001M from Lamberti), 2,2'-bis(2-chlorophenyl)-4,4',5,5'-tetraphenyl-1,2'-bisimidazole (Omnirad BCIM from IGM).

Examples of type II photo-initiators are benzophenone derivatives such as benzophenone (Additol™ BP: UCB), 4-hydroxybenzophenone, 3-hydroxybenzophenone, 4,4'-dihydroxybenzophenone, 2,4,6-trimethylbenzophenone, 2-methylbenzophenone, 3-methylbenzophenone, 4-methylbenzophenone, 2,5-dimethylbenzophenone, 3,4-dimethylbenzophenone, 4-(dimethylamino)benzophenone, [4-(4-methylphenylthio)phenyl]phenyl-methanone, 3,3'-dimethyl-4-methoxy benzophenone, methyl-2-benzoylbenzoate, 4-phenylbenzophenone, 4,4-bis(dimethylamino)benzo-phenone, 4,4-bis(diethylamino)benzophenone, 4,4-bis(ethylmethylamino)benzo-phenone, 4-benzoyl-N,N,N-trimethyl-benzenemethanaminium chloride, 2-hydroxy-3-(4-benzoylphenoxy)-N,N,N-trimethyl-1-propanamium chloride, 4-(13-Acryloyl-1,4,7,10,13-pentaoxamidecyl)benzophenone (Uvecryl™ P36: UCB), 4-benzoyl-N,N-dimethyl-N-[2-(1-oxo-2-propenyl)oy]ethylbenzene-methanaminium chloride, 4-benzoyl-4'-methyldiphenyl sulphide, anthraquinone, ethylanthraquinone, anthraquinone-2-sulfonic acid sodium salt, dibenzosuberenone; acetophenone derivatives such as acetophenone, 4'-phenoxyacetophenone, 4'-hydroxyacetophenone, 3'-hydroxyacetophenone, 3'-ethoxyacetophenone: thioxanthenone derivatives such as thioxanthenone, 2-chlorothioxanthenone, 4-chlorothioxanthenone, 2-isopropylthioxanthenone, 4-isopropylthioxanthenone, 2,4-dimethylthioxanthenone, 2,4-diethylthioxanthenone, 2-hydroxy-3-(3,4-dimethyl-9-oxo-9H-thioxanthon-2-yloxy)-N,N,N-trimethyl-1-propanaminium chloride (Kayacure™ QTX: Nippon Kayaku); diones such as benzyl, camphorquinone, 4,4'-dimethylbenzyl, phenanthrenequinone, phenylpropanedione; dimethylanilines such as 4,4',4"-methylidyne-tris(N,N-dimethylaniline) (Omnirad™ LCV from IGM); imidazole derivatives such as 2,2'-bis(2-chlorophenyl)-4,4',5,5'-tetraphenyl-1,2'-bisimidazole; titanocenes such as bis(eta-5-2,4-cyclopentadiene-1-O-bis-[2,6-difluoro-3-1H-pyrrol-1-yl]phenyl]titanium (Irgacure™ 784; Ciba); iodonium salt such as iodonium, (4-methylphenyl)-[4-(2-methylpropyl-phenyl)-hexafluorophosphate (1-). If desired combinations of photo-initiators may also be used.

For acrylates, diacrylates, triacrylates or multifunctional acrylates, type I photo-initiators are preferred. Especially alpha-hydroxyalkylphenones, such as 2-hydroxy-2-methyl-1-phenyl propan-1-one, 2-hydroxy-2-methyl-1-(4-tert-butyl-) phenylpropan-1-one, 2-hydroxy-[4'-(2-hydroxypropoxy)phenyl]-2-methylpropan-1-one, 2-hydroxy-1-[4-(2-hydroxyethoxy)phenyl]-2-methyl propan-1-one, 1-hydroxycyclohexylphenylketone and oligo[2-hydroxy-2-methyl-1-{4-(1-methylvinyl)phenyl}propanone], alpha-aminoalkylphenones, alpha-sulfonylalkylphenones and acylphosphine oxides such as 2,4,6-trimethylbenzoyl-diphenylphosphine oxide, ethyl-2,4,6-trimethylbenzoyl-phenylphosphinate and bis(2,4,6-trimethylbenzoyl)-phenylphosphine oxide, are preferred.

Cross-linking by infrared radiation is also known as thermal curing. Thus cross-linking may be effectuated by combining the ethylenically unsaturated groups with a free radical initiator and optionally a catalyst and heating the mixture. Exemplary free radical initiators are organic peroxides such as ethyl peroxide and benzyl peroxide; hydroperoxides such as methyl hydroperoxide, acyloins such as benzoin; certain azo compounds such as α,α'-azobisisobutyronitrile and γ,γ'-azobis(γ-cyanovaleric acid); persulfates; peroxosulfates; per-acetates such as methyl peracetate and tert-butyl peracetate; peroxalates such as dimethyl peroxalate and di(tert-butyl) peroxalate; disulfides such as dimethyl thiuram disulfide and ketone peroxides such as methyl ethyl ketone peroxide. Temperatures in the range of from about 23° C. to about 150° C. are generally employed. More often, temperatures in the range of from about 37° C. to about 110° C. are used.

The use of methacrylated recombinant gelatin is especially preferred in combination with a therapeutic protein as pharmaceutical, because cross-linking of methacrylated gelatin can be performed in the presence of a therapeutic protein without co-cross-linking the therapeutic protein and without loss of activity of the therapeutic protein As a result of cross-linking, a controlled release composition comprising a pharmaceutical is obtained. The mesh size or pore size of the obtained product is dependent on the used recombinant gelatin and the cross-linking density. The mesh size is defined as the average distance between two neighbouring cross-links in the hydrogels polymer network. If a therapeutic protein is used as a pharmaceutical, the mesh size can be both larger and smaller than the hydrodynamic radius of the therapeutic protein. The hydrodynamic radius $R_H$ is the apparent radius of a protein in the gelatin matrix taken into account all environmental effects. As such the hydrodynamic radius is derived from the diffusion coefficient D via the relation $D=kT/6\pi\eta R_H$, in which k is Boltzmann's constant, T is the temperature in Kelvin, $\pi$ is 3.14, and $\eta$ is the viscosity of the solution in mPa·s. In the current invention the hydrodynamic radius is preferably measured at physiological conditions. The speed of degradation of the obtained product depends on the amount of cross-links: the more cross-links the slower the degradation. In a preferred embodiment, the speed of degradation is within one year. As release profiles of pharmaceuticals usually extend to a couple of weeks or maximally a few months it is preferable that the matrix consisting of recombinant gelatin degrades in a similar time window. The final charge density of the obtained product depends both on the used amino acid sequence of the recombinant gelatin as well as on the degree of cross-linking. The obtained product can have different appearances, for example dense/homogenous or macroporous. The release profile of the used pharmaceutical can be from several hours (diffusion controlled) to weeks or months (controlled by degradation speed). A combination of both mechanisms can also occur.

As described, the cross-linking can be obtained by cross-linking (meth)acrylate residues introduced in the pre-modification of the recombinant gelatin. However, it is also possible to use a chemical cross-linker that needs not a separate coupling to the used recombinant gelatin. In another embodiment, the invention provides a method for preparing a controlled release composition comprising the steps of:

providing a solution of a recombinant gelatin and a pharmaceutical cross-linking said recombinant gelatin to obtain a three dimensional network structure, wherein said cross-linking is obtained by using a chemical cross-linker selected from water soluble carbodiimide, non-soluble carbodiimide, di-aldehyde di-isocyanate, aldehyde compounds such as formaldehyde and glutaraldehyde, ketone compounds such as diacetyl and chloropentanedion, his (2-chloroethylurea), 2-hydroxy-4,6-dichloro-1,3,5-triazine, reactive halogen-containing compounds disclosed in U.S. Pat. No. 3,288,775, carbamoyl pyridinium compounds in which the pyridine ring carries a sulphate or an alkyl sulphate group disclosed in U.S. Pat. No. 4,063,952 and U.S. Pat. No. 5,529,892, divinylsulfones, and the like. S-triazine derivatives such as 2-hydroxy-4,6-dichloro-s-triazine are well known cross-linking compounds.

Basically the cross-linking occurs between two reactive groups on different gelatin molecules. Particularly preferred is the use of those crosslinkers that are acceptable for medical purposes, in particular water soluble carbodiimide 1-(3-Dimethylaminopropyl)-3-ethylcarbodiimide hydrochloride.

All kinds of pharmaceuticals can be incorporated in the controlled release composition. The term "pharmaceutical" refers to chemical or biological molecules providing a therapeutic, diagnostic, or prophylactic effect preferably in vivo. The term pharmaceutical is also meant to indicate prodrug forms thereof. A "prodrug form" of a pharmaceutical means a structurally related compound or derivative of the pharmaceutical which, when administered to a host is converted into the desired pharmaceutical. A prodrug form may have little or none of the desired pharmacological activity exhibited by the pharmaceutical to which it is converted.

Pharmaceutical ingredients contemplated for use in the compositions described herein include the following categories and examples of drugs and alternative forms of these drugs such as alternative salt forms, free acid forms, free base forms, and hydrates.

Representative examples of pharmaceuticals that may be suitable for use in the controlled release composition the present invention include (grouped by therapeutic class):

Antidiarrhoeals such as diphenoxylate, loperamide and hyoscyamine;

Antihypertensives such as hydralazine, minoxidil, captopril, enalapril, clonidine, prazosin, debrisoquine, diazoxide, guanethidine, methyldopa, reserpine, trimethaphan;

Calcium channel blockers such as diltiazem, felodipine, amlodipine, nitrendipine, nifedipine and verapamil;

Antiarrhythmics such as amiodarone, flecainide, disopyramide, procainamide, mexiletene and quinidine;

Antiangina agents such as glyceryl trinitrate, erythrityl tetranitrate, pentaerythritol tetranitrate, mannitol hexanitrate, perhexylene, isosorbide dinitrate and nicorandil;

Beta-adrenergic blocking agents such as alprenolol, atenolol, bupranolol, carteolol, labetalol, metoprolol, nadolol, nadoxolol, oxprenolol, pindolol, propranolol, sotalol, timolol and timolol maleate;

Cardiotonic glycosides such as digoxin and other cardiac glycosides and theophylline derivatives;

Adrenergic stimulants such as adrenaline, ephedrine, fenoterol, isoprenaline, orciprenaline, rimeterol, salbutamol, salmeterol, terbutaline, dobutamine, phenylephrine, phenylpropanolamine, pseudoephedrine and dopamine;

Vasodilators such as cyclandelate, isoxsuprine, papaverine, dipyrimadole, isosorbide dinitrate, phentolamine, nicotinyl alcohol, co-dergocrine, nicotinic acid, glyceryl trinitrate, pentaerythritol tetranitrate and xanthinol;

Antimigraine preparations such as ergotamine, dihydroergotamine, methysergide, pizotifen and sumatriptan;

Anticoagulants and thrombolytic agents such as warfarin, dicoumarol, low molecular weight heparins such as enoxaparin, streptokinase and its active derivatives;

Hemostatic agents such as aprotinin, tranexamic acid and protamine;

Analgesics and antipyretics including the opioid analgesics such as buprenorphine, dextromoramide, dextropropoxyphene, fentanyl, alfentanil, sufentanil, hydromorphone, methadone, morphine, oxycodone, papaveretum, pentazocine, pethidine, phenoperidine, codeine dihydrocodeine, acetylsalicylic acid (aspirin), paracetamol, and phenazone;

Neurotoxins such as capsaicin;

Hypnotics and sedatives such as the barbiturates amylobarbitone, butobarbitone and pentobarbitone and other hypnotics and sedatives such as chloral hydrate, chlormethiazole, hydroxyzine and meprobamate;

Antianxiety agents such as the benzodiazepines alprazolam, bromazepam, chlordiazepoxide, clobazam, chlorazepate, diazepam, flunitrazepam, flurazepam, lorazepam, nitrazepam, oxazepam, temazepam and triazolam;

Neuroleptic and antipsychotic drugs such as the phenothiazines, chlorpromazine, fluphenazine, pericyazine, perphenazine, promazine, thiopropazate, thioridazine, trifluoperazine; and butyrophenone, droperidol and haloperidol; and other antipsychotic drugs such as pimozide, thiothixene and lithium;

Antidepressants such as the tricyclic antidepressants amitryptyline, clomipramine, desipramine, dothiepin, doxepin, imipramine, nortriptyline, opipramol, protriptyline and trimipramine and the tetracyclic antidepressants such as mianserin and the monoamine oxidase inhibitors such as isocarboxazid, phenelizine, tranylcypromine and moclobemide and selective serotonin re-uptake inhibitors such as fluoxetine, paroxetine, citalopram, fluvoxamine and sertraline;

CNS stimulants such as caffeine and 3-(2-aminobutyl) indole;

Anti-alzheimer's agents such as tacrine;

Anti-Parkinson's agents such as amantadine, benserazide, carbidopa, levodopa, benztropine, biperiden, benzhexyl, procyclidine and dopamine-2 agonists such as S(−)-2-(N-propyl-N-2-thienylethylamino)-5-hydroxytetralin (N-0923);

Anticonvulsants such as phenyloin, valproic acid, primidone, phenobarbitone, methylphenobarbitone and carbamazepine, ethosuximide, methsuximide, phensuximide, sulthiame and clonazepam;

Antiemetics and antinauseants such as the phenothiazines prochloperazine, thiethylperazine and 5HT-3 receptor antagonists such as ondansetron and granisetron, as well as dimenhydrinate, diphenhydramine, metoclopramide, domperidone, hyoscine, hyoscine hydrobromide, hyoscine hydrochloride, clebopride and brompride;

Non-steroidal anti-inflammatory agents including their racemic mixtures or individual enantiomers where applicable, preferably which can be formulated in combination with dermal penetration enhancers, such as ibuprofen, flurbiprofen, ketoprofen, aclofenac, diclofenac, aloxiprin, aproxen, aspirin, diflunisal, fenoprofen, indomethacin, mefenamic acid, naproxen, phenylbutazone, piroxicam, salicylamide, salicylic acid, sulindac, desoxysulindac, tenoxicam, tramadol, ketoralac, flufenisal, salsalate, triethanolamine salicylate, aminopyrine, antipyrine, oxyphenbutazone, apazone, cintazone, flufenamic acid, clonixeril, clonixin, meclofenamic acid, flunixin, coichicine, demecolcine, allopurinol, oxypurinol, benzydamine hydrochloride, dimefadane, indoxole, intrazole, mimbane hydrochloride, paranylene hydrochloride, tetrydamine, benzindopyrine hydrochloride, fluprofen, ibufenac, naproxol, fenbufen, cinchophen, diflumidone sodium, fenamole, flutiazin, metazamide, letimide hydrochloride, nexeridine hydrochloride, octazamide, molinazole, neocinchophen, nimazole, proxazole citrate, tesicam, tesimide, tolmetin, and triflumidate;

Antirheumatoid agents such as penicillamine, aurothioglucose, sodium aurothiomalate, methotrexate and auranofin;

Muscle relaxants such as baclofen, diazepam, cyclobenzaprine hydrochloride, dantrolene, methocarbamol, orphenadrine and quinine;

Agents used in gout and hyperuricaernia such as allopurinol, colchicine, probenecid and sulphinpyrazone;

Oestrogens such as oestradiol, oestriol, oestrone, ethinyloestradiol, mestranol, stilboestrol, dienoestrol, epioestriol, estropipate and zeranol;

Progesterone and other progestagens such as allyloestrenol, dydrgesterone, lynoestrenol, norgestrel, norethyndrel, norethisterone, norethisterone acetate, gestodene, levonorgestrel, medroxyprogesterone and megestrol;

Antiandrogens such as cyproterone acetate and danazol;

Antioestrogens such as tamoxifen and epitiostanol and the aromatase inhibitors, exemestane and 4-hydroxy-androstenedione and its derivatives;

Androgens and anabolic agents such as testosterone, methyltestosterone, clostebol acetate, drostanolone, furazabol, nandrolone oxandrolone, stanozolol, trenbolone acetate, dihydro-testosterone, 17-[alpha]-methyl-19-nortestosterone and fluoxymesterone;

5-alpha reductase inhibitors such as finasteride, turosteride, LY-191704 and MK-306;

Corticosteroids such as betamethasone, betamethasone valerate, cortisone, dexamethasone, dexamethasone 21-phosphate, fludrocortisone, flumethasone, fluocinonide, fluocinonide desonide, fluocinolone, fluocinolone acetonide, fluocortolone, halcinonide, halopredone, hydrocortisone, hydrocortisone 17-valerate, hydrocortisone 17-butyrate, hydrocortisone 21-acetate, methylprednisolone, prednisolone, prednisolone 21-phosphate, prednisone, triamcinolone, triamcinolone acetonide;

Further examples of steroidal antiinflammatory agents such as cortodoxone, fludroracetonide, fludrocortisone, difluorsone diacetate, flurandrenolone acetonide, medrysone, amcinafel, amcinafide, betamethasone and its other esters, chloroprednisone, clorcortelone, descinolone, desonide, dichlorisone, difluprednate, flucloronide, flumethasone, flunisolide, flucortolone, fluoromethalone, fluperolone, fluprednisolone, meprednisone, methylmeprednisolone, paramethasone, cortisone acetate, hydrocortisone cyclopentylpropionate, cortodoxone, flucetonide, fludrocortisone acetate, flurandrenolone acetonide, medrysone, aincinafal, amcinafide, betamethasone, betamethasone benzoate, chloroprednisone acetate, clocortolone acetate, descinolone acetonide, desoximetasone, dichlorisone acetate, difluprednate, flucloronide, flumethasone pivalate, flunisolide acetate, fluperolone acetate, fluprednisolone valerate, paramethasone acetate, prednisolamate, prednival, triamcinolone hexacetonide, cortivazol, formocortal and nivazol;

Pituitary hormones and their active derivatives or analogs such as corticotrophin, thyrotropin, follicle stimulating hormone (FSH), luteinising hormone (LH) and gonadotrophin releasing hormone (GnRH);

Hypoglycemic agents such as insulin, chlorpropamide, glibenclamide, gliclazide, glipizide, tolazamide, tolbutamide and metformin;

Thyroid hormones such as calcitonin, thyroxine and liothyronine and antithyroid agents such as carbimazole and propylthiouracil;

Other miscellaneous hormone agents such as octreotide;

Pituitary inhibitors such as bromocriptine;

Ovulation inducers such as clomiphene;

Diuretics such as the thiazides, related diuretics and loop diuretics, bendrofluazide, chlorothiazide, chlorthalidone, dopamine, cyclopenthiazide, hydrochlorothiazide, indapamide, mefruside, methycholthiazide, metolazone, quinethazone, bumetanide, ethacrynic acid and frusemide and potassium sparing diuretics, spironolactone, amiloride and triamterene;

Antidiuretics such as desmopressin, lypressin and vasopressin including their active derivatives or analogs;

Obstetric drugs including agents acting on the uterus such as ergometrine, oxytocin and gemeprost;

Prostaglandins such as alprostadil (PGE1), prostacyclin (PGI2), dinoprost (prostaglandin F2-alpha) and misoprostol;

Antimicrobials including the cephalosporins such as cephalexin, cefoxytin and cephalothin;

Penicillins such as amoxycillin, amoxycillin with clavulanic acid, ampicillin, bacampicillin, benzathine penicillin, benzylpenicillin, carbenicillin, cloxacillin, methicillin, phenethicillin, phenoxymethylpenicillin, flucloxacillin, meziocillin, piperacillin, ticarcillin and azlocillin;

Tetracyclines such as minocycline, chlortetracycline, tetracycline, demeclocycline, doxycycline, methacycline and oxytetracycline and other tetracycline type antibiotics;

Aminoglycosides such as amikacin, gentamicin, kanamycin, neomycin, netilmicin and tobramycin;

Antifungals such as amorolfine, isoconazole, clotrimazole, econazole, miconazole, nystatin, terbinafine, bifonazole, amphotericin, griseofulvin, ketoconazole, fluconazole and flucytosine, salicylic acid, fezatione, ticlatone, tolnaftate, triacetin, zinc, pyrithione and sodium pyrithione;

Quinolones such as nalidixic acid, cinoxacin, ciprofloxacin, enoxacin and norfloxacin;

Sulphonamides such as phthalysulphthiazole, sulfadoxine, sulphadiazine, sulphamethizole and sulphamethoxazole;

Sulphones such as dapsone;

Other miscellaneous antibiotics such as chloramphenicol, clindamycin, erythromycin, erythromycin ethyl carbonate, erythromycin estolate, erythromycin glucepate, erythromycin ethylsuccinate, erythromycin lactobionate, roxithromycin, lincomycin, natamycin, nitrofurantoin, spectinomycin, vancomycin, aztreonain, colistin IV, metronidazole, tinidazole, fusidic acid, trimethoprim, and 2-thiopyridine N-oxide; halogen compounds, particularly iodine and iodine compounds such as iodine-PVP complex and diiodohydroxyquin, hexachlorophene; chlorhexidine; chloroamine compounds; and benzoylperoxide;

Antituberculosis drugs such as ethambutol, isoniazid, pyrazinamide, rifampicin and clofazimine;

Antimalarials such as primaquine, pyrimethamine, chloroquine, hydroxychloroquine, quinine, mefloquine and halofantrine;

Antiviral agents such as acyclovir and acyclovir prodrugs, famcyclovir, zidovudine, didanosine, stavudine, lamivudine, zalcitabine, saquinavir, indinavir, ritonavir, n-docosanol, tromantadine and idoxuridine;

Anthelmintics such as mebendazole, thiabendazole, niclosamide, praziquantel, pyrantel embonate and diethylcarbamazine;

Cytotoxic agents such as plicainycin, cyclophosphamide, dacarbazine, fluorouracil and its prodrugs (described, for example, in International Journal of Pharmaceutics 111, 223-233 (1994)), methotrexate, procarbazine, 6-mercaptopurine and mucophenolic acid;

Anorectic and weight reducing agents including dexfenfluramine. fenfluramine, diethylpropion, mazindol and phentermine;

Agents used in hypercalcaemia such as calcitriol, dihydrotachysterol and their active derivatives or analogs;

Antitussives such as ethylmorphine, dextromethorphan and pholcodine;

Expectorants such as carbolcysteine, bromhexine, emetine, quanifesin, ipecacuanha and saponins;

Decongestants such as phenylephrine, phenylpropanolamine and pseudoephedrine;

Bronchospasm relaxants such as ephedrine, fenoterol, orciprenaline, rimiterol, salbutamol, sodium cromoglycate, cromoglycic acid and its prodrugs (described, for example, in International Journal of Pharmaceutics 7, 63-75 (1980)), terbutaline, ipratropium bromide, salmeterol and theophylline and theophylline derivatives;

Antihistamines such as meclozine, cyclizine, chlorcyclizine, hydroxyzine, brompheniramine, chlorpheniramine, clemastine, cyproheptadine, dexchlorpheniramine, diphenhydramine, diphenylamine, doxylamine, mebhydrolin, pheniramine, tripolidine, azatadine, diphenylpyraline, methdilazine, terfenadine, astemizole, loratidine and cetirizine;

Local anaesthetics such as bupivacaine, amethocaine, lignocaine, lidocaine, cinchocaine, dibucaine, mepivacaine, prilocaine, etidocaine, veratridine (specific c-fiber blocker) and procaine;

Stratum corneum lipids, such as ceramides, cholesterol and free fatty acids, for improved skin barrier repair [Man, et al. J. Invest. Dermatol., 106(5), 1096, (1996)];

Neuromuscular blocking agents such as suxamethonium, alcuronium, pancuronium, atracurium, gallamine, tubocurarine and vecuronium;

Smoking cessation agents such as nicotine, bupropion and ibogaine;

Insecticides and other pesticides which are suitable for local application;

Dermatological agents, such as vitamins A, C, B1, B2, B6, B12a and E, vitamin E acetate and vitamin E sorbate;

Allergens for desensitisation such as house, dust or mite allergens;

Nutritional agents, such as vitamins, essential amino acids and fats;

Keratolytics such as the alpha-hydroxy acids, glycolic acid and salicylic acid;

The controlled release composition of the present invention is particularly advantageous for the encapsulation/incorporation of macromolecular pharmacologically active agents such as proteins, enzymes, peptides, polysaccharides, nucleic cells, tissues, and the like. Immobilization of macromolecular pharmaceuticals into a controlled release composition can be difficult due to the ease with which some of these macromolecular agents denature when exposed to organic solvents, some constituents present in bodily fluids or to temperatures appreciably higher than room temperature. However, since the method of the present invention, as well as the controlled release composition formed by the method utilize biocompatible solvents such as water, DMSO or ethanol, and furthermore does not require heating, the risk of the denaturation of these types of materials is reduced. Furthermore, due to the size of these macromolecular pharmaceuticals, these agents become trapped in the hydrogel that forms upon implantation of controlled release composition, and thereby are protected from constituents of bodily fluids that would otherwise denature them. Thus, the controlled release devices of the present invention allow these macromolecular agents may exert their therapeutic effects, while yet protecting them from denaturation or other structural degradation.

Examples of cells which can be utilized as pharmaceutical/pharmacologically active agent in the drug delivery device of the present invention include primary cultures as well as established cell lines, including transformed cells. Examples of these include, but are not limited to pancreatic islet cells, human foreskin fibroblasts, Chinese hamster ovary cells, beta cell insulomas, lymphoblastic leukemia cells, mouse 3T3 fibroblasts, dopamine secreting ventral mesencephalon cells, neuroblastoid cells, adrenal medulla cells, T-cells combinations of these, and the like. As can be seen from this partial list, cells of all types, including dermal, neural, blood, organ, muscle, glandular, reproductive and immune system cells, as well as cells of all species of origin, can be encapsulated successfully by this method.

In a more preferred embodiment, said pharmaceutical is a therapeutic protein. Examples of proteins which can be incorporated into the drug delivery device of the present invention include, but are not limited to, hemoglobin, vasporessin, oxytocin, adrenocorticocotrophic, hormone, epidermal growth factor, prolactin, luliberin or luteinising hormone releasing factor, human growth factor, basic fibroblast growth, hepatocyte growth factor, angiogenesis growth factor, vascular endothelial growth factor, bone morphogenetic growth factor, nerve growth factor, and the like; interleukines, enzymes such as adenosine deaminase, superoxide dismutase, xanthine oxidase, and the like; enzyme systems; blood clotting factors; clot inhibitors or clot dissolving agents such as streptokinase and tissue plasminogen activator; antigens for immunization; hormones; polysaccharides such as heparin; oligonucleotides; bacteria and other microbial microorganisms including viruses; monoclonal antibodies; vitamins; cofactors; retroviruses for gene therapy, combinations of these and the like.

The use of a recombinant gelatin based controlled release composition together with a therapeutic protein as pharmaceutical is a very useful embodiment of the present invention. In principle every recombinant gelatin can be genetically modified to fit the used therapeutic protein, for example by introducing certain charges in the recombinant gelatin to strengthen the binding of the used therapeutic protein to the controlled release composition. For every therapeutic protein a suitable environment can be created.

The method as described herein, i.e. a method for preparing a controlled release composition comprising the steps of providing a solution of a recombinant gelatin and a pharmaceutical and (chemically) cross-linking said recombinant gelatin to obtain a three dimensional network structure, can be performed with at least one kind/type of recombinant gelatin but can also be performed by using at least two kinds/types of recombinant gelatin (preferably with different characteristics). Moreover, combinations of a recombinant gelatin with at least one water-soluble polymer (preferably biodegradable, potentially cross-linking and not being a recombinant, gelatin) are also possible. Without limiting the scope of the above invention these biodegradable polymers can be natural or synthetic or made by recombinant techniques. Examples are dextrans, hyaluronic acid, poly-lactic acid, poly-glycolic acid, or copolymers of those, chitin, chitosan, alginate, polyesters, etc. Further suitable polymers are disclosed in US 2004/0235161 on pg 2. Also the amount of cross-linkers can be varied from at least one or at least two to more than two (for example three or four).

Furthermore addition of adjuvants like buffers, salts, surfactants, humectants and co-solvents in the preparation process can also be used.

Also the amount and kinds of used pharmaceuticals can be varied, for example the use of at least two therapeutic proteins or the use of a therapeutic protein in combination with an antibiotic.

Another embodiment of the invention is a controlled release composition comprising at least a chemically cross-linked recombinant gelatin and a pharmaceutical. Such a controlled release composition is for example obtainable by the method described herein.

In a preferred embodiment, the invention provides a controlled release composition comprising at least a chemically cross-linked recombinant gelatin and a pharmaceutical, in which said recombinant gelatin is human or human-like. By using human or human-like recombinant gelatin, there is no risk for animal diseases (such as prion disease from bovine origin) and there is also no risk of immunogenic response (in contrast to natural collagen).

Human-like gelatin is defined as being for at least 60%, more preferable for at least 80%, most preferably for at least 90% identical to amino acid sequence of gelatin in human collagen. A starting point for preparing a recombinant human or human-like gelatin is for example the human Col1A1 sequence. However, it is also possible to use other human collagen sequences to start with. Recombinant human gelatin is defined herein as gelating having a human amino acid sequence, a level of glycosylation equal to human gelatin as well as a level of hydroxylation equal to the human gelatin. Human-like gelatin refers to recombinant gelatin having one or more mutations in the amino acid sequence of the protein, an altered level of glycosylation relative to endogenous human levels (preferably lowered in order to reduce immunoigenicity of the recombinant gelatin), and/or altered level of hydroxuylation of lysine and/or proline residues relative to endogenous human levels. Mammalian-like is the corresponding term for mammalian-derived gelatins.

The chemically cross-linked recombinant gelatin is for example obtained by chemically modifying the recombinant gelatin with a cross-linkable group, i.e. the invention provides a controlled release composition comprising at least a chemically cross-linked recombinant gelatin and a pharmaceutical, wherein said recombinant gelatin is chemically modified with a cross-linkable group. Preferably, said cross-linkable group is selected from the group of acrylates and even more preferably said cross-linkable group is a methacrylate. In yet another embodiment, said chemical cross-linked recombinant gelatin is obtained by using a chemical cross-linker selected from water soluble carbodiimide, non-soluble carbodiimide, formaldehyde, di-aldehyde and di-isocyanate.

The controlled release composition described herein can subsequently be used in the preparation of a pharmaceutical composition. In yet another embodiment, the invention thus provides a pharmaceutical composition comprising a controlled release composition, wherein said controlled release composition comprises at least a chemically cross-linked recombinant gelatin and a pharmaceutical. Such a pharmaceutical composition can further comprise an adjuvant or diluent. Examples of suitable pharmaceutical compositions are an injectable formulation, a subdermal delivery depot, a dressing, or an implant (gel or moulded gel). An example of an injectable formulation is a formulation comprising (matrix) particles of 1-500 µm as described in EP 1 801 122.

The herein described controlled release composition can also be used in the preparation of a pharmaceutical article and the invention thus also provides a pharmaceutical article comprising a controlled release composition, wherein said controlled release composition comprises at least a chemically cross-linked recombinant gelatin and a pharmaceutical. Examples of suitable articles are implants such as a stent or an artificial vascular graft, a bone implant or an insoluble drug particle, wound dressings, skin grafts.

A pharmaceutical composition according to the invention can be administered via any route, i.e. via injection (for example subcutaneous, intravenous or intramuscular) or via surgical implantation, orally, via inhalation or via an external wound dressing or even transdermal.

As disclosed in the present invention, a recombinant gelatin is extremely useful in the production of a network structure suitable for controlled release. In yet another embodiment, the invention provides the use of a recombinant gelatin for producing a controlled release composition.

The invention further provides a method for treating a subject in need thereof, comprising providing said subject with an effective amount of a controlled release composition, i.e. a controlled release composition comprising at least a chemically cross-linked recombinant gelatin and a pharmaceutical. Treatments that could be more effective using controlled release systems are for example: pain treatment, cancer therapy, cardiovascular diseases, myocardial repair, angiogenesis, bone repair and regeneration, wound treatment, neural stimulation/therapy, diabetics, and the like. The controlled release composition can be administered by injection (subcutaneous, intravenous or intramuscular) or orally or via inhalation. However, the used controlled release composition can also be implanted via surgery. Yet another suitable route of administering is via an external wound dressing or even trans dermally.

The invention further provides use of a controlled release composition as described herein for the preparation of a medicament for the treatment of pain, cancer therapy, cardiovascular diseases, myocardial repair, angiogenesis, bone repair and regeneration, wound treatment, neural stimulation/therapy or diabetics.

The invention will be explained in more detail in the following, non-limiting examples.

Experimental Part

In the present invention, recombinant gelatins were used for preparing hydrogels for the controlled release of proteins. In one embodiment methacrylate residues were coupled to recombinant gelatin to enable chemical cross-linking. The methacrylated gelatins were analyzed by $^1$H-NMR to determine the degree of substitution (DS), and by SDS-PAGE to determine purity. Furthermore, enzymatic degradability was tested by incubating gelatin solutions in the presence of matrix-metalloproteinases 1 and 9. Hydrogels were formed by radical polymerization using potassium peroxodisulfate (KPS) and N,N,N',N'-tetramethylethylenediamine (TEMED) as initiators. Also gelatin microspheres as obtained by methods as described in EP 1 801 122 were subjected to biodegradation by collagenases.

The release of the model 'therapeutic' protein lysozyme from recombinant gelatin hydrogels was studied. The chemical stability of the released proteins was determined by HPLC, and protein functionality was assessed by measuring enzymatic activity.

Materials and Methods

Recombinant HU4 gelatin (MW 72.6 kDa) and CBE (17.2 kDa) were used. The preparation of these recombinant gelatins is described elsewhere (EP-A-1398324, EP-A-0926543 and EP-A-1014176). FIG. 1 shows the amino acid sequence of HU4 gelatin. The amino acid sequence of the repeating blocks corresponds to a part of the α1 chain of human type I collagen. FIG. 2 shows the amino acid sequence of recombinant gelatin CBE. This sequence is based on human type I collagen and contains an increased number of RGD motifs. Further more an acid treated hydrolysed porcine gelatin (average MW 26 kDa, polydispersity D 1.6, DGF Stoess and a hydrolysed alkali-treated bovine gelatin (average MW 23 kDa, polydispersity D 1.6, Nitta) were used. Molecular weight and polydispersity were determined by GPC using a TSKgel superSW3000 and 2000 column with as eluens 10 mM $Na_2SO_4$, 1% SDS, pH 5.3.

Methacrylic anhydride (MA-Anh) was purchased from Sigma-Aldrich (St. Louis, Mo.). Potassium peroxodisulfate (KPS) was obtained from Merck (Darmstadt, Germany). Stock solutions with 20 mg/ml KPS were prepared with isotonic phosphate buffer of pH 7.4, aliquoted in Eppendorf tubes, and stored at $-20°$ C. N,N,N',N'-tetramethylethylenediamine (TEMED) was obtained from Fluka (Buchs, Switzerland). Stock solutions with 20% (v/v) TEMED were prepared in isotonic phosphate buffer of pH 7.4, aliquoted in Eppendorf tubes, and stored at $-20°$ C. Hen egg lysozyme was obtained from Fluka (Buchs, Switzerland). Stock solutions with 10 mg/ml lysozyme were prepared in isotonic phosphate buffer of pH 7.4, filtered through 0.2 mm HPLC filters (Alltech, Deerfield, Ill.), aliquoted in low binding Eppendorf tubes (Eppendorf, Hamburg, Germany), and stored at $-20°$ C. The protein concentration of the stock solutions was determined by UV absorption at 280 nm (e280 lysozyme=37000 $M^{-1}\cdot cm^{-1}$). Physiological phosphate buffer was prepared by dissolving 0.76 mg/ml $NaH_2PO_4\times H_2O$, 0.79 mg/ml $Na_2HPO_4$, and 0.06 mg/ml NaCl, adjusting the pH to 7.4 with NaOH solution, and filtering the buffer solution through 0.2 mm filters (Schleicher and Schuell, Dassel, Germany). 4-Aminophenolmercuric acetate (APMA) and human fibroblast matrix metalloproteinases 1 and 9 (MMP1 and MMP9) were obtained from Sigma-Aldrich (St. Louis, Mo.).

A) Methacrylation of (Recombinant) Gelatin

Rec. gelatins HU4 and CBE, an acid treated porcine gelatin (as obtained from PB) and an alkali-treated bovine gelatin (as obtained from Nitta) were derivatized with methacrylate residues as follows. 2.5 g gelatin was dissolved in 200 ml phosphate buffer of pH 7.4. Solutions under a nitrogen atmosphere were heated to 50° C. and methacrylic-anhydride (MA-Anh) was added. To achieve different degrees of substitution, the MA-Anh:gelatin ratio was varied. During the methacrylation reaction, the pH of the solution was regularly controlled and, if necessary, kept between 7 and 7.4 by the addition of 1 M NaOH solution. After vigorous stirring at 50° C. for one hour, the solutions were extensively dialyzed against water (dialysis tubes with 14 kDa MWCO Medicell International, London, UK). Dried products were obtained by lyophilization and were stored in sealed glass containers at 4° C.

B) Determination of Degree of Substitution (DS)

The degree of substitution (DS), i.e. the fraction of methacrylated amino acids with respect to the total number of primary amine groups of the recombinant gelatin, was determined by $^1$H-NMR. Measurements were performed with a Gemini spectrometer (Varian Associates, Inc. NMR Instruments, Palo Alto, Calif.) operating at 300 MHz. Samples were prepared by dissolving 40 mg/ml gelatin in deuterium oxide. Forty scans were accumulated using a 62.5° pulse and 2 seconds relaxation delay. Integration of the phenylalanine signal and division of its area by the known number of phenylalanine protons gelatin molecule gave the area of one proton. Dividing the total area of the two methacrylate signals by the area of one proton gave the number of protons that made up the methacrylate signals. This value, divided by two, corresponded to the average number of methacrylate residues per gelatin chain and enabled the calculation of DS.

C) Preparation of Hydrogels

Hydrogels with an initial gelatin concentration of 20% (w/w) were prepared. Methacrylated gelatin was dissolved in phosphate buffer of pH 7.4 containing 0.05% $NaN_3$, and solutions were centrifuged (5 min, 10000 RPM). Upon centrifugation, 596 mg gelatin solution was filled in an Eppendorf tube, and 75 microliter phosphate buffer of pH 7.4 (or Lysozyme stock solution for release experiments) were added and gently mixed. KPS 20 mg/ml stock solution (56.5 microlitere) and TEMED 20% stock solution (22.5 microliter) were added and mixed to induce cross-linking of the gelatin methacrylate residues. The solution was filled in 1 ml syringes (Becton-Dickinson, Franklin Lake, N.J.). After 1.5 h, the syringes were opened to remove the hydrogels, which were cut into cylinders of 6 min length and 2.3 mm radius.

D) Lysozyme Release Experiments and Activity Determination

Hydrogel cylinders loaded with protein were placed in glass vials containing 3 ml phosphate buffer of pH 7.4 with 0.05% $NaN_3$. The vials were stored in a shaking water bath at 37° C. At different time-points, 1 ml of the phosphate buffer was sampled, filled in low-binding Eppendorf tubes, and stored at −20° C. until analysis. The removed volume was replaced by fresh phosphate buffer solution. Samples were analyzed by HPLC using an Alltima C18 RP-HPLC column (Alltech, Deerfield, Ill.). The injection volume was 40 microliter. A linear gradient was run that changed the starting mixture of 70% eluent A (10% acetonitrile, 90% water, 0.1% trifluoroacetic acid) and 30% eluent B (90% acetonitrile, 10% water, 0.1% trifluoroacetic acid) to 55% eluent A and 45% eluent B in 15 min. Return to the starting eluent composition occurred in one minute. Detection was by UV absorption at 280 nm, and protein concentration was determined by the area under the curve (AUC) of the HPLC signals using standards prepared from the protein stock solutions.

Samples from release experiments with lysozyme were also analyzed by an enzymatic activity assay. 50 microliter sample were added to a cuvette containing 1.3 ml of a 0.2 mg/ml *M. luteus* suspension in phosphate buffer of pH 6.2. Lysis of *M. luteus* by lysozyme led to a linear decrease of the optical density (OD) of the suspension, which was detected at 450 nm using a spectrophotometer (Lambda 2, Perkin Elmer, Wellesley, Mass.). The concentration of enzymatically active lysozyme was determined from the slope of the OD decrease with time using standards prepared from the lysozyme stock solution.

E) Enzymatic Biodegradation of the Gelatins and Hydrogels MMP1/MMP9

The ability of recombinant gelatin to act as substrates for the matrix metalloproteinases 1 and 9 (MMP1 and MMP9) was tested by incubating gelatin solutions in the presence of enzyme. Prior to incubation, MMP's (2.5 mg/ml) were activated at 37° C. in 0.05 M TRIS buffer of pH 7.4 containing 0.15 M NaCl, 1 mM 4-aminophenolmercuric acetate (APMA), 0.01 M $CaCl_2$, and 0.001 mM $ZnCl_2$ for 5 h. Solutions with 4 mg/ml gelatin were prepared using the same TRIS buffer. Activated MMP1 or MMP9 was added to the gelatin solutions such that the enzyme concentration was 2 mg/ml and the gelatin concentration 0.8 mg/ml. Solutions were incubated at 37° C. for 6 days, and samples were drawn at different time points. After 5 days, fresh MMP solution was added, yielding a total enzyme concentration of 2.2 mg/ml and a gelatin concentration of 0.44 mg/ml for the last day of incubation. All samples were diluted to a gelatin concentration of 0.44 mg/ml and kept at −20° C. until analysis by size exclusion chromatography (SEC) using a Superdex 200 column (GE Healthcare Europe GmBH, Roosendaal, The Netherlands). Isotonic phosphate buffer of pH 7.4 was used as an eluent. Twenty microliters of sample were injected and the flow-rate was 0.4 ml/min. Detection was by UV absorption at 210 nm.

CHC

Degradation of recombinant gelatin hydrogel particles by collagenase *clostridium histolyticum* (CHC). A suspension of recombinant gelatin hydrogel spheres of ca 100 μm which are cross-linked by EDC (as obtained by methods as described in EP 1 801 122) was subjected to treatment by CHC. After 24 hrs the presence of remaining gelatin particles was visually observed Results The results of the release experiments as conducted above are summarized in table I.

TABLE I

Fraction and activity of lysozyme released from gelatin hydrogels (20% gelatin, degree of substitution DS = 1)

| Gelatin type | Gelatin concentration | DS | Percent released | Activity of the released lysozyme in % of non-captured lysozym |
|---|---|---|---|---|
| Rec. Gelatin HU4 | 20% | 1 | 86 | 98 |
| Rec. Gelatin CBE | 20% | 1 | 90 | 97 |
| Porcine Gelatin | 20% | 1 | 75 | 90 |
| Bovine Gelatin | 20% | 1 | 50 | 89 |

The results in table I clearly indicate that the use of recombinant gelatins result in a higher activity of the released lysozyme. Hence, the invention also provides a method to increase the activity of a pharmaceutical (for example a therapeutic protein) in a controlled release composition, comprising preparing said controlled release composition with a recombinant gelatin. Apparently the pure and homogeneous character of the recombinant gelatins and the hydrogels made thereof preserve the three dimensional network structure and hence the enzymatic activity of the lysozyme model protein very well. Furthermore it can be concluded that the cross-linking of the methacrylate residues has no adverse effect on the released lysozyme.

Another aspect of the invention that is demonstrated in table I is the higher amount of released lysozyme in case of recombinant gelatins. It is speculated that due to the homogeneity of the recombinant gelatin hydrogels almost no proteins are trapped in the hydrogel, whereas in case of natural gelatins with their broad molecular weight distribution high density area's in the hydrogel are present in which these proteins are trapped.

The results of the in vitro biodegradation test of HU4 with various degrees of substitution level (DS) by MMP-1 and MMP-9 are shown in Table II. In table III the in vitro degradation test of (recombinant) gelatin particles by CHC is shown

TABLE II biodegradation of rec. gelatins by MMP-1 and MMP-9

| Gelatin type | DS | Degradation by MMP-1 | Degradation by MMP-9 |
|---|---|---|---|
| Rec. Gelatin HU4 | 0 | + | − |
| Rec. Gelatin HU4 | 1 | + | − |

TABLE III

In vitro biodegradation of cross-linked rec. gelatins particles by CHC

| Gelatin type | Degradation by CHC |
|---|---|
| Rec. Gelatin HU4 | + |
| Rec. Gelatin CBE | + |
| Porcine gelatin | + |
| Bovine gelatin | + |

+ means no particles visible, indicative for being degraded

The results in table II and III clearly illustrate that recombinant gelatins and natural gelatins are well-biodegradable which is a premiss to be used in controlled release compositions. For the recombinant gelatins this was a surprising result since the sequence did not comprise a known cleavage site.

DESCRIPTION OF FIGURES

Figure 1:
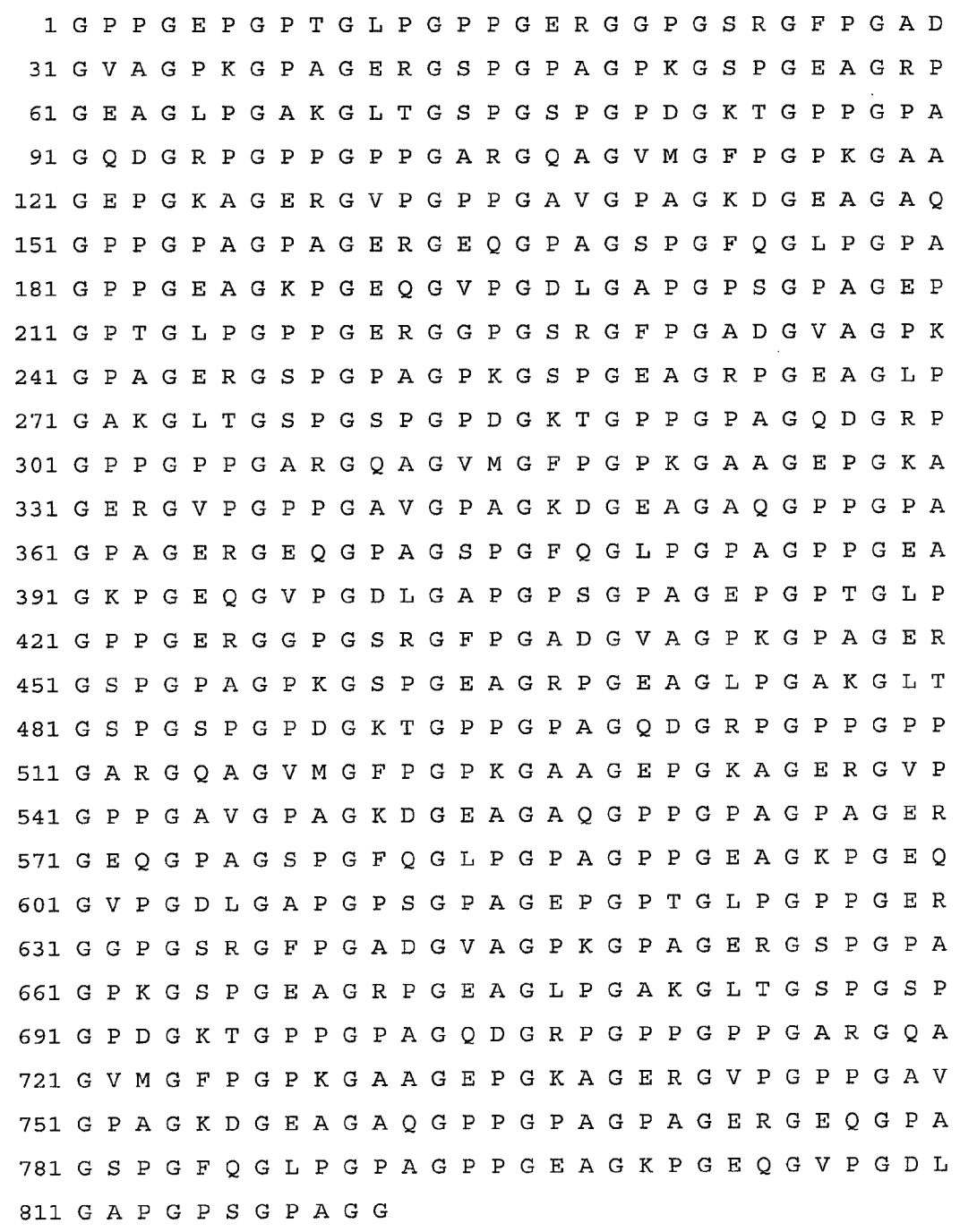

FIG. 1
Amino acid sequence of HU4 gelatin.
FIG. 2
Amino acid sequence of CBE.
FIG. 3
Human Col1A1.

The invention claimed is:

1. A method for preparing a controlled release composition comprising the steps of:
providing a mixture comprising a recombinant gelatin and a pharmaceutical;
cross-linking said recombinant gelatin in said mixture to provide a three dimensional network structure wherein the said pharmaceutical is entrapped;
wherein said recombinant gelatin is essentially free of hydroxylysine crosslinks and/or hydroxyproline residues.

2. A method according to claim 1, further comprising drying the obtained three dimensional network structure wherein the said pharmaceutical is entrapped.

3. A method according to claim 1, wherein said recombinant gelatin is chemically modified with a cross-linkable group.

4. A method according to claim 3, wherein said recombinant gelatin is chemically modified with a methacrylate cross-linkable group.

5. A method according to claim 1, wherein the recombinant gelatin has essentially no glycosylation.

6. A method according to claim 1 wherein the recombinant gelatin has essentially no glycosylation and the cross-linked gelatin is obtained by redox polymerisation or radical polymerisation, wherein the redox polymerisation or radical polymerisation is initiated by a mixture of potassium peroxodisulfate and N,N,N',N' tetramethylethyenediamine.

7. A method according to claim 6 wherein said recombinant gelatin has a molecular weight of between about 2.5 to about 100 kD.

8. A method according to claim 1, wherein the cross-linked gelatin is obtained by redox polymerisation, radical polymerisation or chemical cross-linking.

9. A method according to claim 2, wherein the cross-linked gelatin is obtained by redox polymerisation, radical polymerisation or chemical cross-linking.

10. A method according to claim 3, wherein the cross-linked gelatin is obtained by redox polymerisation, radical polymerisation or chemical cross-linking.

11. A method according to claim 4, wherein the cross-linked gelatin is obtained by redox polymerisation, radical polymerisation or chemical cross-linking.

12. A method according to claim 8, wherein the redox polymerisation or radical polymerisation is initiated by a mixture of potassium peroxodisulfate and N,N,N',N' tetramethylethyenediamine.

13. A method according to claim 9, wherein the redox polymerisation or radical polymerisation is initiated by a mixture of potassium peroxodisulfate and N,N,N',N' tetramethylethyenediamine.

14. A method according to claim 10, wherein the redox polymerisation or radical polymerisation is initiated by a mixture of potassium peroxodisulfate and N,N,N',N' tetramethylethyenediamine.

15. A method according to claim 11, wherein the redox polymerisation or radical polymerisation is initiated by a mixture of potassium peroxodisulfate and N,N,N',N' tetramethylethyenediamine.

16. A controlled release composition comprising a pharmaceutical and at least a chemically cross-linked recombinant gelatin essentially free of hydroxylysine crosslinks and/or hydroxyproline residues.

17. A controlled release composition according to claim 16, in which said recombinant gelatin has essentially no glycosylation.

18. A controlled release composition according to claim 16, wherein said recombinant gelatin has a molecular weight of between about 2.5 to about 100 kD.

19. A controlled release composition according to claim 16, in which said recombinant gelatin is a methacrylated recombinant gelatin.

* * * * *